US012637678B2

(12) United States Patent
Liu et al.

(10) Patent No.: US 12,637,678 B2
(45) Date of Patent: May 26, 2026

(54) ANTI-FIBROTIC COMPOSITIONS COMPRISING FENDRR OR FRAGMENTS OR VARIANTS THEREOF AND METHODS OF PRODUCTION AND USE THEREOF

(71) Applicant: The Board of Regents for the Oklahoma Agricultural and Mechanical Colleges, Stillwater, OK (US)

(72) Inventors: Lin Liu, Edmond, OK (US); Chaoqun Huang, Stillwater, OK (US)

(73) Assignee: The Board of Regents for the Oklahoma Agricultural and Mechanical Colleges, Stillwater, OK (US)

( * ) Notice: Subject to any disclaimer, the term of this patent is extended or adjusted under 35 U.S.C. 154(b) by 0 days.

(21) Appl. No.: 18/361,305

(22) Filed: Jul. 28, 2023

(65) Prior Publication Data

US 2024/0018525 A1 Jan. 18, 2024

Related U.S. Application Data

(62) Division of application No. 17/082,617, filed on Oct. 28, 2020, now abandoned.

(60) Provisional application No. 62/926,797, filed on Oct. 28, 2019.

(51) Int. Cl.
| | |
|---|---|
| *C12N 15/113* | (2010.01) |
| *A61P 11/00* | (2006.01) |
| *A61P 35/00* | (2006.01) |
| *C12N 7/00* | (2006.01) |
| *C12N 15/86* | (2006.01) |

(52) U.S. Cl.
CPC .......... *C12N 15/1138* (2013.01); *A61P 11/00* (2018.01); *A61P 35/00* (2018.01); *C12N 7/00* (2013.01); *C12N 15/86* (2013.01); *C12N 2310/14* (2013.01); *C12N 2320/35* (2013.01); *C12N 2740/15043* (2013.01); *C12N 2750/14143* (2013.01)

(58) Field of Classification Search
CPC ...... C12N 15/1138; C12N 7/00; C12N 15/86; C12N 2310/14; C12N 2320/35; C12N 2740/15043; C12N 2750/14143; C12N 15/113; C12N 2310/111; A61P 11/00; A61P 35/00
See application file for complete search history.

(56) References Cited

U.S. PATENT DOCUMENTS

2017/0268008 A1 9/2017 Khalil et al.

OTHER PUBLICATIONS

Huang et al. "Interaction of long noncoding RNAs and microRNAs in the pathogenesis of idiopathic pulmonary fibrosis." Physiological genomics 47.10 (2015): 463-469 (Year: 2015).*
NCBI Gene ID: 406996 (Year: 2009).*
Yu-An Huang et al. "Predicting lncRNA-miRNA interaction via graph convolution auto-encoder." Frontiers in genetics 10 (2019): 758 (Year: 2019).*
Senavirathna, et al.; "Hypoxia and Transforming Growth Factor β1 Regulation of Long Non-Coding RNA Transcriptomes in Human Pulmonary Fibroblasts," Physiological Reports (2020) 8:e14343, 16 pages.
Huang, et al.; "Long Noncoding Rna Fendrr Exhibits Antifibrotic Activity in Pulmonary Fibrosis," American Journal of Respiratory Cell and Molecular Biology (2020), 62(4):440-453.
Munteanu, et al.; "Long Non-Coding RNA FENDRR Regulates IFNγ-Induced M1 Phenotype in Macrophages," Scientific Reports (2020) 10:13672; 12 pages.
Woeller, et al.; "Out of Tune: Fibroblasts Turn Fibrotic When They Lack a FENDRR," American Journal of Respiratory Cell and Molecular Biology (2020), 62(4): 403-404.

* cited by examiner

*Primary Examiner* — Alexander W Nicol
(74) *Attorney, Agent, or Firm* — Dunlap Codding, P.C.

(57) ABSTRACT

Compositions containing long non-coding RNAs (lncRNA's) or fragments or variants thereof are disclosed. Also disclosed are compositions containing vectors that include or encode the lncRNA's or fragments/variants thereof. Further disclosed are methods of producing and using these compositions containing or encoding the lncRNA's.

5 Claims, 11 Drawing Sheets
(9 of 11 Drawing Sheet(s) Filed in Color)

Specification includes a Sequence Listing.

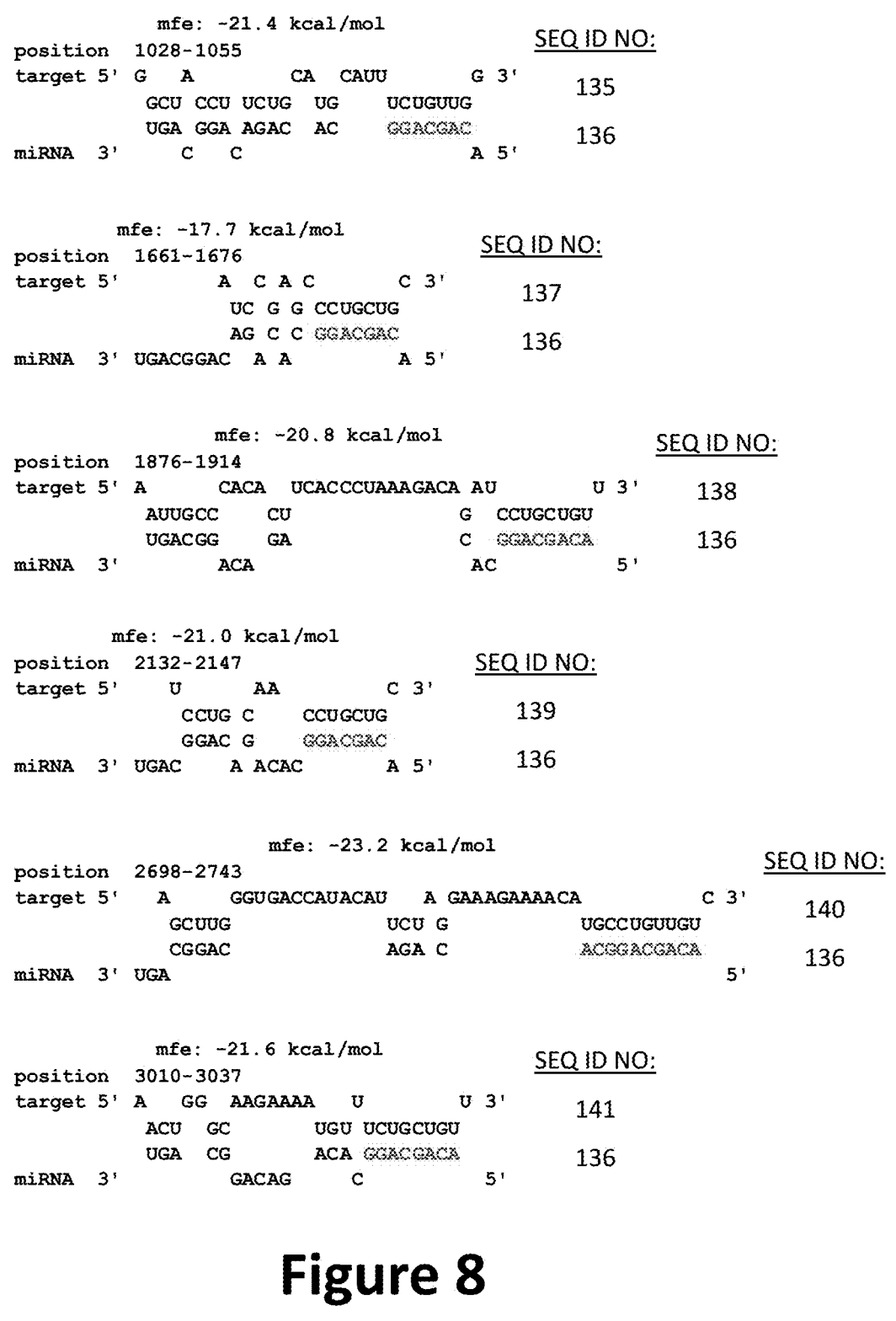

```
                 mfe: -21.4 kcal/mol
                                                SEQ ID NO:
position  1028-1055
target 5' G   A          CA  CAUU          G 3'       135
             GCU CCU UCUG  UG     UCUGUUG
             UGA GGA AGAC  AC     GGACGAC            136
miRNA   3'       C   C                     A 5'
```

```
              mfe: -17.7 kcal/mol
                                            SEQ ID NO:
position  1661-1676
target 5'        A  C A C         C 3'          137
                UC G G CCUGCUG
                AG C C GGACGAC                  136
miRNA   3' UGACGGAC  A A          A 5'
```

```
                 mfe: -20.8 kcal/mol
                                                  SEQ ID NO:
position  1876-1914
target 5' A       CACA  UCACCCUAAAGACA AU         U 3'    138
            AUUGCC     CU              G  CCUGCUGU
            UGACGG     GA              C  GGACGACA        136
miRNA   3'       ACA                  AC            5'
```

```
            mfe: -21.0 kcal/mol
                                         SEQ ID NO:
position  2132-2147
target 5'    U       AA        C 3'         139
           CCUG C    CCUGCUG
           GGAC G    GGACGAC                136
miRNA   3' UGAC    A ACAC      A 5'
```

```
               mfe: -23.2 kcal/mol
                                                       SEQ ID NO:
position  2698-2743
target 5'    A      GGUGACCAUACAU   A GAAAGAAAACA          C 3'   140
            GCUUG              UCU G         UGCCUGUUGU
            CGGAC              AGA C         ACGGACGACA           136
miRNA   3' UGA                                             5'
```

```
            mfe: -21.6 kcal/mol
                                         SEQ ID NO:
position  3010-3037
target 5' A   GG  AAGAAAA   U        U 3'    141
           ACU  GC       UGU UCUGCUGU
           UGA  CG       ACA GGACGACA        136
miRNA   3'        GACAG    C        5'
```

Figure 8

ANTI-FIBROTIC COMPOSITIONS COMPRISING FENDRR OR FRAGMENTS OR VARIANTS THEREOF AND METHODS OF PRODUCTION AND USE THEREOF

CROSS REFERENCE TO RELATED APPLICATIONS/INCORPORATION BY REFERENCE STATEMENT

The subject application is a divisional of U.S. Ser. No. 17/082,617, filed Oct. 28, 2020; which claims benefit under 35 USC § 119(e) of provisional application U.S. Ser. No. 62/926,797, filed Oct. 28, 2019. The entire contents of the above-referenced patent applications are hereby expressly incorporated herein by reference.

STATEMENT REGARDING FEDERALLY SPONSORED RESEARCH OR DEVELOPMENT

This invention was made with U.S. Government support under Grant Nos. R01HL135152, R01HL116876, and P20GM103648 awarded by the National Institutes of Health. The Government has certain rights in this invention.

REFERENCE TO SEQUENCE LISTING SUBMITTED ELECTRONICALLY

The instant application contains, as a separate part of the present disclosure, a Sequence Listing which has been submitted via Patent Center in computer readable form as an XML file. The Sequence Listing, created Jul. 27, 2023 is named "57910214_ Sequence_Listing.xml" and is 149,770 bytes in size. The entire contents of the Sequence Listing are hereby incorporated herein by reference.

BACKGROUND

Idiopathic Pulmonary Fibrosis (IPF) is a chronic and lethal fibrotic lung disease characterized by scarring of lung tissues and worsening lung function. Historically, lung tissues from IPF patients show similar characteristics as usual interstitial pneumonia (UIP). The disease primarily occurs in individuals between the ages of 50 and 70 and more frequently occurs in men. The course of IPF is difficult to predict, with a median survival time of 3 to 5 years after diagnosis; there is currently no effective therapy.

The human genome generates more non-coding RNAs (ncRNAs) than protein-coding RNA sequences. Long non-coding RNAs (lncRNAs) are ncRNAs that are typically longer than 200 nt and are transcribed from DNA that was once thought to be "junk." These RNAs are larger than small ncRNAs such as microRNAs, Piwi-interacting RNAs, siR-NAs, and small nucleolar RNAs, which are typically about 20-180 nt in length. Current estimates suggest that about 20,000 distinct lncRNAs are present in humans.

Most ncRNAs, including long non-coding RNAs (lncR-NAs), are synthesized by polymerase II. lncRNAs are mRNA-like transcripts, but are non-protein encoding RNA molecules that are more than 200 bp long. lncRNAs are processed by capping, splicing, and polyadenylation, which is similar to the process of protein-coding genes. Only a small number of lncRNAs have been annotated functionally. lncRNAs are located in the nucleus, cytoplasm, and mitochondria, where they participate in various molecular functions, such as chromatin remodeling, transcriptional regulation, RNA splicing, RNA stability, and translation control. lncRNAs are important in controlling critical physiological functions, including gene imprinting, cell proliferation, differentiation, apoptosis, autophagy, migration, immune responses, and chromosome structure. Aberrant expression of lncRNAs has been associated with a broad range of human diseases, including cardiovascular, neurodegenerative, metabolic, and lung diseases, as well as tumors and infections.

Fetal-lethal noncoding developmental regulatory RNA (FENDRR) is a lncRNA that is transcribed bidirectionally with FOXF1 on its opposite strand. FENDRR binds to polycomb repressive complex 2 (PRC2) and/or TrxG/MLL complexes to epigenetically regulate the expression of its target genes. Murine Fendrr is essential for normal development of the lungs, heart, and body wall. LacZ reporter profiling has shown that Fendrr is highly expressed in embryonic and adult lung tissue. Fendrr homozygotes are embryonic-lethal due to defective structural maturation of the lungs. Genomic deletion within the FENDRR gene was found in a human fatal lung development disorder, alveolar capillary dysplasia with misalignment of pulmonary veins (ACD/MPV). FENDRR has been linked to other human diseases, such as gastric cancer.

Therefore, there is a need in the art for new and improved compositions that contain or encode lncRNAs, such as (but not limited to), FENDRR. There is also a need in the art for methods of inhibiting activation of fibroblasts and treating or reducing the occurrence of pulmonary fibrosis. It is to such compositions and methods that the present disclosure is directed.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 8. miR-214 binding sites in human FENDRR tran-script variant 3.

DETAILED DESCRIPTION

Figure 1:
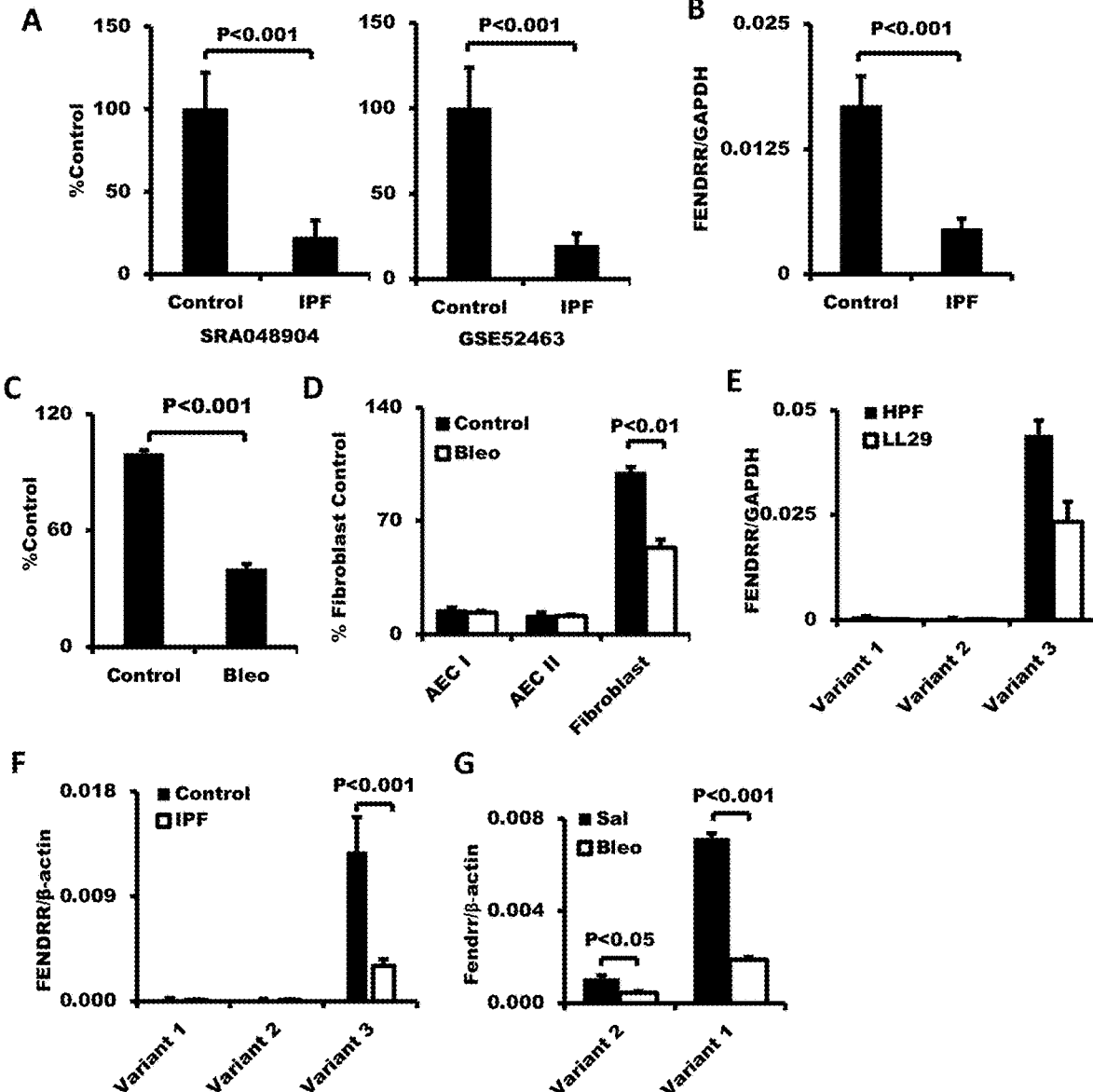
FIG. 1. FENDRR was down-regulated in fibrotic lungs and fibroblasts. Panel (A): Next-generation RNA sequencing analysis showing the down-regulation of FENDRR in IPF lungs in two published datasets. Panel (B): Real-time PCR showing FENDRR down-regulation in LTRC IPF lungs. n=7 for Control, n=27 for IPF. The primers detecting human FENDRR transcript variant 2 and 3 were used. Panel (C): Real-time PCR showing FENDRR down-regulation in fibrotic mouse lungs (n=3). Panel (D): Real-time PCR showing FENDRR expression in primary fibroblasts and alveolar epithelial type I and type II cells (AEC I and AEC II) isolated from saline (Sal)- and bleomycin (Bleo)-treated mice (n=3). The expression levels were normalized to GAPDH. Data are expressed as the percent of the fibroblast control group. The primers detecting mouse Fendrr transcript variants 1 and 2 were used for C and D. Panel (E) shows the copy number of human FENDRR transcript variants in the fibroblasts, as determined by absolute quantitative Real-time PCR (n=3). Panel (F) shows the copy number of human FENDRR variants in LTRC IPF lungs, as determined by droplet digital PCR. n=7 for Control, n=27 for IPF. Panel (G) shows the copy number of mouse Fendrr variants in the lungs of control and bleomycin-treated mice, as determined by droplet digital PCR (n=3). The results are presented as the means±SEM. Student's t-test for A, B, and C and ANOVA, followed by Tukey's HSD test for D, F, and G.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which this presently disclosed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed herein can be made and executed without undue experimentation in light of the present disclosure. While the compositions and methods of the inventive concept(s) have been described in terms of particular embodiments, it will be apparent to those of skill in the art that variations may be applied to the compositions and/or methods and in the steps or in the sequence of steps of the methods described herein without departing from the concept, spirit, and scope of the inventive concept(s). All such similar substitutions and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. For example, the term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "polypeptide" as used herein will be understood to refer to a polymer of amino acids. The polymer may include d-, l-, or artificial variants of amino acids. In addition, the term "polypeptide" will be understood to include peptides, proteins, and glycoproteins.

The term "polynucleotide" as used herein will be understood to refer to a polymer of two or more nucleotides. Nucleotides, as used herein, will be understood to include deoxyribose nucleotides and/or ribose nucleotides, as well as artificial variants thereof. The term polynucleotide also includes single-stranded and double-stranded molecules.

The terms "analog" or "variant" as used herein will be understood to refer to a variation of the normal or standard form or the wild-type form of molecules. For polypeptides or polynucleotides, an analog may be a variant (polymorphism), a mutant, and/or a naturally or artificially chemically modified version of the wild-type polynucleotide (including combinations of the above). Such analogs may have higher, full, intermediate, or lower activity than the normal form of the molecule, or no activity at all. Alternatively and/or in addition thereto, for a chemical, an analog may be any structure that has the desired functionalities (including alterations or substitutions in the core moiety), even if comprised of different atoms or isomeric arrangements.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "pharmaceutically acceptable" refers to compounds, compositions, and/or dosage forms which are, with the scope of sound medical judgment, suitable for administration to humans and/or animals without undue adverse side effects such as (but not limited to) toxicity, irritation, and/or allergic response commensurate with a reasonable benefit/risk ratio.

The phrase "pharmaceutically-acceptable carrier" as used herein means a pharmaceutically-acceptable material, composition, excipient, or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. The term "pharmaceutically-acceptable carrier" refers to any carrier, vehicle, excipient, and/or diluent known in the art or otherwise contemplated herein that may improve solubility, deliverability, dispersion, stability, and/or conformational integrity of the compositions disclosed herein.

The term "patient" as used herein includes human and veterinary subjects. "Mammal" for purposes of treatment refers to any animal classified as a mammal, including (but not limited to) humans, domestic and farm animals, nonhuman primates, and any other animal that has mammary tissue.

The term "child" is meant to refer to a human individual who would be recognized by one of skill in the art as an infant, toddler, etc., or an individual less than about 18 years of age, usually less than about 16 years of age, usually less than about 14 years of age, or even less (e.g., from newborn to about 2, about 3, about 4, about 5, about 6, about 7, about 8, about 9, about 10, about 11, or about 12 years of age). The term "elderly" generally refers to a human individual whose age is greater than about 50 years of age, usually greater than about 55 years of age, frequently greater than about 60 years of age or more (e.g., about 65 years of age and upwards).

The term "treatment" refers to both therapeutic treatment and prophylactic or preventative measures. Those in need of treatment include, but are not limited to, individuals already having a particular condition/disease/infection as well as individuals who are at risk of acquiring a particular condition/disease/infection (e.g., those needing prophylactic/preventative measures). The term "treating" refers to administering an agent to a patient for therapeutic and/or prophylactic/preventative purposes.

A "therapeutic composition" or "pharmaceutical composition" refers to an agent that may be administered in vivo to bring about a therapeutic and/or prophylactic/preventative effect. Administering a therapeutically effective amount or prophylactically effective amount is intended to provide a therapeutic benefit in the treatment, prevention, and/or management of a disease, condition, and/or infection. The specific amount that is therapeutically effective can be readily determined by the ordinary medical practitioner, and can vary depending on factors known in the art, such as (but not limited to) the type of condition/disease/infection, the patient's history and age, the stage of the condition/disease/infection, and the co-administration of other agents.

The term "effective amount" refers to an amount of a biologically active molecule or conjugate or derivative thereof sufficient to exhibit a detectable therapeutic effect without undue adverse side effects (such as but not limited to) toxicity, irritation, and allergic response) commensurate with a reasonable benefit/risk ratio when used in the manner of the inventive concept(s). The therapeutic effect may include, for example but not by way of limitation, preventing, inhibiting, or reducing the occurrence of pulmonary fibrosis. The effective amount for a subject will depend upon the type of subject, the subject's size and health, the nature and severity of the condition/disease/infection to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy," and will be understood to mean that the patient in need of treatment is treated or given another drug for the condition/disease/infection in conjunction with the pharmaceutical compositions of the present disclosure. This concurrent therapy can be sequential therapy, where the patient is treated first with one pharmaceutical composition and then the other pharmaceutical composition, or the two pharmaceutical compositions are given simultaneously.

The terms "administration" and "administering," as used herein, will be understood to include all routes of administration known in the art, including but not limited to, oral, topical, transdermal, parenteral, subcutaneous, intranasal, intratracheal, intrabronchial, mucosal, intramuscular, intraperitoneal, intravitreal, and intravenous routes, and including both local and systemic applications. In addition, the compositions of the present disclosure (and/or the methods of administration of same) may be designed to provide delayed, controlled, or sustained release using formulation techniques which are well known in the art.

Turning now to the inventive concept(s), certain non-limiting embodiments thereof are directed to an anti-fibrotic composition that comprises an isolated and/or purified Fetal-lethal noncoding developmental regulatory RNA (FENDRR) lncRNA or a fragment or variant thereof and a pharmaceutically-acceptable carrier. In certain non-limiting embodiments, the FENDRR lncRNA or fragment/variant thereof is encoded by a sequence comprising at least about 100 contiguous nucleotides of at least one of SEQ ID NOS:1-3 and 133-134, or a sequence that differs from at least one of SEQ ID NOS:1-3 and 133-134 by less than about 30 amino acids. SEQ ID NO:1 represents Human FENDRR transcript variant 1 (GenBank Accession No. NR_036444), SEQ ID NO:2 is Human FENDRR transcript variant 2 (GenBank Accession No. NR_033925), and SEQ ID NO:3 represents a novel Human FENDRR transcript variant 3 disclosed herein (GenBank Accession No. MK522493.1). SEQ ID NO:133 represents mouse FENDRR transcript variant 1 (GenBank Accession No. NR_130109), while SEQ ID NO:134 represents mouse FENDRR transcript variant 2 (GenBank Accession No. NR_045471).

The fragment/variant of FENDRR lncRNA may be at least about 25 contiguous nucleotides long, such as (but not limited to) at least about 50, at least about 60, at least about 70, at least about 80, at least about 90, at least about 100, at least about 110, at least about 120, at least about 130, at least about 140, at least about 150, at least about 160, at least about 170, at least about 180, at least about 190, at least about 200, at least about 210, at least about 220, at least about 230, at least about 240, at least about 250, at least about 260, at least about 270, at least about 280, at least about 290, at least about 300, at least about 310, at least about 320, at least about 330, at least about 340, at least about 350, at least about 360, at least about 370, at least about 380, at least about 390, at least about 400, at least about 425, at least about 450, at least about 475, at least about 500, at least about 525, at least about 550, at least about 575, at least about 600, at least about 650, at least about 700, at least about 750, at least about 800, at least about 850, at least about 900, at least about 950, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, at least about 2500, at least about 2600, at least about 2700, at least about 2800, at least about 2900, at least about 3000, at least about 3100, or at least about 3200 nucleotides long, or the like. The scope of the present disclosure also includes fragments/variants of FENDRR lncRNA that have a length within a range of two of the above values (i.e., a range of from about 50 to about 500 nucleotides long, a range of from about 100 to about 150 nucleotides long, etc.), as well as a length that falls between two of any of the above values (i.e., at least about 725, at least about 1450, etc.).

In a particular (but non-limiting) embodiment, the fragment or variant of FENDRR lncRNA may comprise any of the regions outlined in Table 4, such as, but not limited to the region between 1419-1549. However, it will be understood that these "regions" are for purposes of example only, and the fragment or variant may include additional sequence on one or both sides thereof.

The fragment or variant of FENDRR lncRNA may be encoded by a sequence that differs from at least one of SEQ ID NOS:1-3 and 133-134 by less than about 30 amino acids, such as, but not limited to, less than about 29 amino acids, less than about 28 amino acids, less than about 27 amino acids, less than about 26 amino acids, less than about 25 amino acids, less than about 24 amino acids, less than about 23 amino acids, less than about 22 amino acids, less than about 21 amino acids, less than about 20 amino acids, less than about 19 amino acids, less than about 18 amino acids, less than about 17 amino acids, less than about 16 amino acids, less than about 15 amino acids, less than about 14 amino acids, less than about 13 amino acids, less than about 12 amino acids, less than about 11 amino acids, less than about 10 amino acids, less than about 9 amino acids, less than about 8 amino acids, less than about 7 amino acids, less than about 6 amino acids, less than about 5 amino acids, and the like.

The FENDRR lncRNA or fragment or variant thereof may be modified and/or encapsulated so as to improve the stability thereof. Any nucleotide modifications or encapsulation methods known in the art or otherwise contemplated herein may be utilized in accordance with the present disclosure. For example (but not by way of limitation), the FENDRR lncRNA or fragment or variant thereof may be modified by one of more modifications selected from a PS backbone modification, 2'-OMe, 2'-F, 2'MOE, a sugar substitution, LNA, and/or L-RNA modification.

In addition (but not by way of limitation), the FENDRR lncRNA or fragment/variant thereof may be encapsulated in a delivery vehicle. Non-limiting examples of delivery vehicles that may be utilized in accordance with the present disclosure include a liposome, a lipoplex, a microvesicle, an exosome, a lipidoid nanoparticle, a polymeric nanoparticle, an inorganic nanoparticle, and a stable nucleic acid particle (SNALP), and the like, as well as variations, derivatives, and combinations thereof.

Certain non-limiting embodiments of the present disclosure are directed to a pharmaceutical composition that comprises a vector comprising a sequence encoding at least about 100 contiguous nucleotides of a Fetal-lethal noncoding developmental regulatory RNA (FENDRR) lncRNA or a fragment or variant thereof and a pharmaceutically-acceptable carrier.

Any sequences encoding FENDRR lncRNAs or fragments/variants thereof that are known in the art or otherwise contemplated herein may be utilized in accordance with the present disclosure. In certain non-limiting embodiments, the sequence comprises at least about 100 contiguous nucleotides of at least one of SEQ ID NOS:1-3 and 133-134, or a sequence that differs from at least one of SEQ ID NOS:1-3 and 133-134 by less than about 30 amino acids.

Any vectors known in the art or otherwise contemplated herein may be utilized in accordance with the present disclosure, so long as the vector allows for expression of the FENDRR lncRNA or fragment/variant thereof. Non-limiting examples of vectors that can be utilized in accordance with the present disclosure include an adenoviral vector, an adeno-associated viral (AAV) vector, an alpha viral vector, a herpes viral vector, a lentiviral vector, a measles viral vector, a pox viral vector, a phage vector, a retroviral vector, and the like.

The vector can include any other components/elements that aid the vector in functioning in accordance with the present disclosure. For example (but not by way of limitation), the vector may further include an expression control sequence to which the FENDRR sequence is operably linked.

Any pharmaceutically-acceptable carriers known in the art or otherwise contemplated herein may be utilized in accordance with the present disclosure. Non-limiting examples include a pharmaceutically acceptable solvent, suspending agent, or vehicle that aid in delivery of the compositions of the present disclosure to the human or animal. The carrier may be liquid or solid and is selected with the planned manner of administration in mind. Examples of pharmaceutically acceptable carriers that may be utilized in accordance with the present disclosure include, but are not limited to, PEG, liposomes, ethanol, DMSO, aqueous buffers, oils, DPPC, lipids, other biologically-active molecules, vaccine-adjuvants, and combinations thereof. In addition, in certain particular (but non-limiting) examples, pharmaceutically-acceptable carriers can also contain a physiologically acceptable compound that acts to stabilize the compound and/or increase or decrease the absorption or clearance rates of the pharmaceutical compositions. Physiologically acceptable compounds can include (for example, but not by way of limitation) carbohydrates, such as glucose, sucrose, or dextrans; antioxidants, such as ascorbic acid or glutathione; chelating agents; low molecular weight proteins; detergents; liposomal carriers; and/or excipients or other stabilizers and/or buffers. Other physiologically acceptable compounds include (for example, but not by way of limitation) wetting agents, emulsifying agents, dispersing agents, and/or preservatives.

The compositions of the present disclosure may be provided in any form and any formulation that allows the compositions to function in accordance with the present disclosure. For example (but not by way of limitation), the compositions may be in solid (such as, but not limited to, tablets, powders, and dry powder inhalers), liquid (such as, but not limited to, emulsions, microemulsions, solutions, suspensions, syrups, and elixirs), or gels, or sprays, mists, or aerosols.

Certain non-limiting embodiments of the present disclosure are directed to a method of inhibiting activation of lung fibroblasts. In the method, the lung fibroblasts are contacted with any of the compositions disclosed or otherwise contemplated herein. For example (but not by way of limitation), the composition may be selected from: (i) an isolated and/or purified Fetal-lethal noncoding developmental regulatory RNA (FENDRR) lncRNA or a fragment or variant thereof (as described in detail herein above or otherwise contemplated herein); and/or (ii) a vector comprising a sequence encoding at least about 100 contiguous nucleotides of a Fetal-lethal noncoding developmental regulatory RNA (FENDRR) lncRNA or a fragment or variant thereof (as described in detail herein above or otherwise contemplated herein). In particular (but not by way of limitation): in (i), the FENDRR lncRNA is encoded by a sequence comprising at least about 100 contiguous nucleotides of at least one of SEQ ID NOS:1-3 and 133-134, or a sequence that differs from at least one of SEQ ID NOS:1-3 and 133-134 by less than about 30 amino acids; and in (ii), the sequence comprises at least about 100 contiguous nucleotides of at least one of SEQ ID NOS:1-3 and 133-134, or a sequence that differs from at least one of SEQ ID NOS:1-3 and 133-134 by less than about 30 amino acids.

Certain non-limiting embodiments of the present disclosure are directed to a method of treating or reducing the occurrence of pulmonary fibrosis (such as, but not limited to, idiopathic pulmonary fibrosis) in a subject. In the method, any of the compositions disclosed or otherwise contemplated herein may be administered to the subject. For example (but not by way of limitation), the composition may be selected from: (i) a composition comprising a Fetal-lethal noncoding developmental regulatory RNA (FENDRR) lncRNA or a fragment or variant thereof and a pharmaceutically-acceptable carrier (as described in detail herein above or otherwise contemplated herein); or (ii) a composition comprising a vector and a pharmaceutically-acceptable carrier, wherein the vector comprises a sequence encoding at least about 100 contiguous nucleotides of a Fetal-lethal noncoding developmental regulatory RNA (FENDRR) lncRNA or a fragment or variant thereof (as described in detail herein above or otherwise contemplated herein). In particular (but not by way of limitation): in (i), the FENDRR lncRNA is encoded by a sequence comprising at least about 100 contiguous nucleotides of at least one of SEQ ID NOS:1-3 and 133-134, or a sequence that differs from at least one of SEQ ID NOS:1-3 and 133-134 by less than about 30 amino acids; and in (ii), the sequence comprises at least about 100 contiguous nucleotides of at least one of SEQ ID NOS:1-3 and 133-134, or a sequence that differs from at least one of SEQ ID NOS:1-3 and 133-134 by less than about 30 amino acids.

In the methods of the present disclosure, the compositions may be administered in therapeutically effective amounts. An effective amount is a dosage of the composition sufficient to provide a therapeutically or medically desirable result or effect in the subject to which the composition is administered. The effective amount will vary with the particular condition being treated, the age and physical condition of the subject being treated, the severity of the condition, the duration of the treatment, the nature of the concurrent or combination therapy (if any), the specific route of administration, and like factors within the knowledge and expertise of the health practitioner. For example, in connection with methods directed towards treating subjects having a condition characterized by pulmonary fibrosis, an effective amount would be an amount sufficient to mitigate, reduce, modulate, inhibit, or otherwise effectively treat the condition in the subject.

Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount is typically, but not limited to, an amount in a range from 0.1 μg/kg to about 2000 mg/kg, or from 1.0 μg/kg to about 1000 mg/kg, or from about 0.1 mg/kg to about 500 mg/kg, or from about 1.0 mg/kg to about 100 mg/kg, in one or more dose administrations daily, for one or more days. If desired, the effective daily dose of the active compound may be administered as two, three, four, five, six, or more sub-doses, for example, administered separately at appropriate intervals throughout the day, optionally, in unit dosage forms. In some embodiments, the inhibitors are administered for more than 7 days, more than 10 days, more than 14 days, or more than 20 days. In still other embodiments, the inhibitor is administered over a period of weeks or months. In still other embodiments, the inhibitor is delivered on alternate days. For example, the agent may be delivered every two days, or every three days, or every four days, or every five days, or every six days, or every week, or every month.

The compounds of the presently disclosed inventive concepts may be administered alone or in combination with one or more additional therapies and may be administered by a variety of administration routes. The particular mode selected will depend, of course, upon the compound selected, the condition being treated, the severity of the condition, whether the treatment is therapeutic or prophylactic, and the dosage required for efficacy. The methods of the present disclosure, generally speaking, may be practiced using any mode of administration that is medically acceptable, meaning any mode that produces effective levels of the active compounds without causing clinically unacceptable adverse effects. Non-limiting examples of administration routes that may be utilized in accordance with the present disclosure include oral, topical, transdermal, parenteral, subcutaneous, intranasal, intratracheal, intrabronchial, mucosal, intramuscular, intraperitoneal, intravitreal, and/or intravenous routes, and the like.

For example (but not by way of limitation), the composition can be administered to the pulmonary tract by any methods known in the art or otherwise contemplated herein. For example, but not by way of limitation, commercially available devices are known for many different methods and mechanisms of delivering various liquid or aerosolized pharmaceutical formulations to pulmonary tissue, including (but not limited to), intranasal instillation devices, intratracheal instillation devices, intratracheal injection devices, dry powder inhalers (DPIs), pressurized metered dose inhalers (pMDIs), nebulizers (such as, but not limited to, pneumatic (jet) nebulizers and electromechanical nebulizers), electrohydrodynamic aerosol devices, insufflators, respirators, and the like. These devices can include a single dose or multiple doses of the compositions of the present disclosure.

In addition, the formulations of the compositions of the present disclosure may include one or more additional components/elements that aid in the administration of the compositions, as based upon the delivery device. For example (but not by way of limitation), pMDIs, DPIs, and nebulizers typically employ one or more propellants to propel the liquid or cloud of dry powder formulation out of the device, to form an aerosol, and/or to atomize the liquid formulation. Any suitable propellants/pressurized gas supplies may be utilized. The propellant may take a variety of forms. For example, the propellant may be a compressed gas or a liquefied gas. Aerosol formulations for use in the subject method typically include (for example, but not by way of limitation) propellants, surfactants, and/or co-solvents. Suitable liquid compositions comprise the active ingredient in an aqueous, pharmaceutically acceptable inhalant solvent such as (but not limited to) isotonic saline or bacteriostatic water. Suitable liquid formulations for nasal sprays or nasal drops typically include (for example, but not by way of limitation) aqueous or oily solutions of the active ingredient.

When the compositions are formulated for being inhaled, the inhaled formulation may be designed for application to the upper (such as, but not limited to, the nasal cavity, pharynx, and larynx) and/or lower respiratory tract (such as, but not limited to, the trachea, bronchi, and lungs). Different devices and excipients can be used depending on whether the application is to the upper and/or lower respiratory tract and can be determined by those skilled in the art.

EXAMPLE

An Example is provided hereinbelow. However, the present disclosure is to be understood to not be limited in its application to the specific experimentation, results, and laboratory procedures disclosed herein. Rather, the Example is simply provided as one of various embodiments and is meant to be exemplary, not exhaustive.

In the present Example, FENDRR was identified as a down-regulated lncRNA in the lungs of IPF patients. In addition, the functional roles and underlying mechanisms of FENDRR in pulmonary fibrosis were further determined. The results of this Example showed that FENDRR inhibited the activation of lung fibroblasts by binding iron-responsive element-binding protein 1 (IRP1) to control iron levels and by competing with the pro-fibrotic miR-214. This Example also demonstrated that FENDRR functions as an anti-fibrotic lncRNA in vivo.

Materials and Methods

RNA-seq analyses: Two next-generation RNA sequencing datasets from the lung tissues of IPF patients are publicly available from NCBI's Sequence Read Archive (SRA accession number SRA048904) and NCBI's Gene Expression Omnibus (GEO Series accession number GSE52463). These datasets were re-analyzed to identify altered lncRNAs in IPF lungs. RNAs from 3 normal and 3 IPF patient lungs were sequenced in the SRA048904 datasets. RNAs from 7 normal and 8 IPF patient lungs were sequenced in the GSE52463 datasets. These datasets were re-analyzed to identify altered lncRNAs in IPF lungs. Paired-end reads were directionally mapped to the genomic loci of lncRNA (GRCh37/hg19) by TopHat2 (https://ccb.jhu.edu/software/tophat/manual.shtml). CuffDiff analysis was then performed to identify the dysregulated lncRNAs (cole-trapnell-lab.github.io/cufflinks/). lncRNAs with a log 2-fold change and a False Discovery Rate (FDR)<0.05 were considered to be differentially expressed.

IPF lung tissues and RNA isolation: Twenty-seven IPF patient lung tissue samples were obtained from Lung Tissue Research Consortium (LTRC). All of the samples were submerged in RNAlater solution and stored at −80° C. before use. Total RNA was isolated from these human lung tissues, murine lung tissues or cells using Tri Reagents (Molecular Research Center, Cincinnati, OH). Cytoplasmic and nuclear RNAs were isolated from the cytoplasmic and nuclear fractions of human lung fibroblasts, which were separated using a Cytoplasmic & Nuclear RNA Purification Kit (Norgen Biotek Corp, Thorold, ON, Canada) (Catalog #21000). The RNA concentration and quality were determined with a NanoDrop ND-1000 Spectrophotometer (NanoDrop Tech., Rockland, DE) with an $A_{260}/A_{280}$ ratio>1.8 and an $A_{260}/A_{230}$ ratio>1.7.

Cell culture: HEK 293T cells and human lung fibroblasts (HFL1, CCD-8Lu, and LL29) were purchased from the American Type Culture Collection (ATCC) (Manassas, VA, USA). HEK 293A cells were purchased from Invitrogen. HFL1 cells were human diploid fibroblasts derived from fetal lungs. CCD-8Lu and LL29 cells were human fibroblasts isolated from the lungs of a healthy adult and an IPF patient, respectively. The cells were grown and maintained with the following media supplemented with 10% fetal bovine serum (FBS): HFL1, and LL29 cells, F12K Medium (Kaighn's Modification of Ham's F-12 Medium); and CCD-8Lu, Eagle's Minimum Essential Medium. Primary human pulmonary fibroblasts (HPF) were purchased from Promo-Cell (Heidelberg, Germany). HPF cells were cultured in fibroblast medium with its supplements (PromoCell, Heidelberg, Germany).

Isolation of mouse lung fibroblasts: Primary lung fibroblasts were isolated from the lungs of saline- or bleomycin-treated mice according to a previously described protocol (1). The cells were cultured in DMEM containing 10% FBS and used at passages 3-9. Alveolar epithelial type II cells were also isolated from these mice and differentiated into alveolar epithelial type I cells, as previously described (2). Real-Time PCR Relative real-time PCR: The mRNA and lncRNA expression levels were determined by SYBR Green I-based real-time PCR. One microgram of DNase-treated total RNA was reverse-transcribed into cDNA with random primers and oligo dT. The real-time PCR thermal conditions were 95° C. for 10 min, followed by 40 cycles of 95° C. for 15 sec and 60° C. for 60 sec. Glyceraldehyde-3-phosphate dehydrogenase (GAPDH) or β-actin were used as internal controls. The microRNA expression levels were determined by Real-time PCR as previously described (3). The sequences of the primers used for real-time PCR are shown in Table 1.

TABLE 1

Primers for Real-Time PCR

| Name | Sequence | SEQ ID NO: |
|---|---|---|
| Human | | |
| NR_033925-FENDDR-FW (variant 1) | CGCACAGACCCAGGATTACTTC | 4 |
| NR_033925-FENDDR-RE (variant 1) | GCTCCTTATGCAAGCATTCTTCA | 5 |
| NR_036444-FENDDR-FW (variant 2) | CCCTGCTCCTCTCGAATTTCT | 6 |
| NR_036444-FENDDR-RE (variant 2) | CCATGCACCAAATCCTTAAAATGT | 7 |
| MK522493-FENDDR-FW (variant 3) | CAGAAGCCCCCTCCTGTTATC | 8 |
| MK522493-FENDDR-RE (variant 3) | AAGAAGCCAAGCCCATTCTGT | 9 |
| FENDRR-FW (variant 2, 3) | GCGCACAGACCCAGGATTT | 10 |
| FENDRR-RE (variant 2, 3) | ACACGGGCAGAGCTGGTTT | 11 |
| hCOL1A1-FW | CGAAGACATCCCACCAATCAC | 12 |
| hCOL1A1-RE | CAGATCACGTCATCGCACAAC | 13 |
| hCOL3A1-FW | TGGCTACTTCTCGCTCTGCTT | 14 |
| hCOL3A1-RE | TTCCAGACATCTCTATCCGCATAG | 15 |
| hαSMA-FW | GTGTTGCCCCTGAAGAGCAT | 16 |

TABLE 1-continued

Primers for Real-Time PCR

| Name | Sequence | SEQ ID NO: |
|---|---|---|
| hαSMA-RE | CGCCTGGATAGCCACATACAT | 17 |
| hGAPDH-FW | GAAGGTGAAGGTCGGAGTCAAC | 18 |
| hGAPDH-RE | CATGGGTGGAATCATATTGGAA | 19 |
| hACTB-FW | GGCACCACACCTTCTACAATGA | 20 |
| hACTB-RE | ACAGCCTGGATAGCAACGTACA | 21 |
| hU2snRNA-FW | CATCGCTTCTCGGCCTTTTG | 22 |
| hU2snRNA-RE | TGGAGGTACTGCAATACCAGG | 23 |
| hTFRC-FW | ATCCGGTTACTGGGCAATTTC | 24 |
| hTFRC-RE | TCTGTGTCCTCGCAAAAACAG | 25 |
| mature miR-214 | ACAGCAGGCACAGACAGGCA | 26 |
| pri-miR-214-FW | CCCTTTCCCCTTACTCTCCAA | 27 |
| pri-miR-214-RE | GGATGTTCTGCACAGCAAGT | 28 |
| *Mouse* | | |
| NR_130109-Fendrr-FW (variant 1) | GAACTCAGGACCTCTGGAAGA | 29 |
| NR_130109-Fendrr-RE (variant 1) | GGTCTGCCTTGTCGTTTTCTT | 30 |
| NR_045471-Fendrr-FW (variant 2) | TGCTGAATGGAGGCATCTACA | 31 |
| NR_045471-Fendrr-RE (variant 2) | GCTTGAACCGTCTCTCCTTTG | 32 |
| FENDRR-FW (variant 1, 2) | CACGATCCCAGGTGGACTTG | 33 |
| FENDRR-RE (variant 1, 2) | TGCAGGAGTGAAGGGTGTCTCT | 34 |
| mCOL1A1-FW | ACGCATGGCCAAGAAGACAT | 35 |
| mCOL1A1-RE | TTGTGGCAGATACAGATCAAGCA | 36 |
| mCOL3A1-FW | CACCCTTCTTCATCCCACTCTT | 37 |
| mCOL3A1-RE | TGACATGGTTCTGGCTTCCA | 38 |
| mGAPDH-FW | CTCGTCCCGTAGACAAAATGGT | 39 |
| mGAPDH-RE | TGATGGCAACAATCTCCACTTT | 40 |

Absolute real-time PCR: The expression levels of FENDRR transcript variants were also determined by using the SYBR Green I-based real-time PCR. Conventional PCR products were amplified and purified with gel extraction, and copy numbers were calculated to construct standard curves ($10^3$-$10^8$ copies). A standard curve was plotted with threshold cycle (CT) versus the logarithmic value of the gene copy number. The RNA copy numbers of unknown samples were generated directly from the standard curves with Sequence Detector software provided by the 7500 Fast Real-Time PCR system. All copy numbers were normalized to GAPDH mRNA.

Droplet digital PCR: Droplet digital PCR: The expression of FENDRR variants were also determined by QX200 AutoDG droplet digital PCR (ddPCR) system (Bio-Rad, Hercules, CA) according to the manufacturer's instructions. The ddPCR reaction mixture consisted of the QX200™ ddPCR™ EvaGreen Supermix, forward and reverse primer (200 nM), and 5 μl cDNA in a total reaction volume of 20 μl. Droplets were generated in 8-well cartridges using the automated droplet generator. After completion of the droplet generation, water-in-oil emulsions were transferred to a 96-well plate, and PCR was performed using a C1000 Touch™ thermal cycler. Thermal cycling conditions were 95° C. for 5 min, followed by 40 cycles at 95° C. for 30 secs, 60° C. for 1 min with a final 5 min at 90° C. After PCR amplification, fluorescence intensities of each droplet from the samples were measured using the QX200 droplet reader. Positive droplets containing amplification products were distinguished from negative droplets and counted by applying a fluorescence amplitude threshold in QuantaSoft software Version 1.7.4.0917. QuantaSoft software provides copies of a gene per microliter (copies/μl). The number of copies of a gene per template cDNA was calculated as copies/μl×20 (μl). The copy number of FENDNR variants were normalized to that of β-actin. The primers used are listed in Table 1.

Construction of plasmids: FENDRR and miR-214 expression vectors: FENDRR was amplified by PCR using specific primers (Table 2) from human lung tissue cDNA. Mature miR-214 plus ~200 bp flanking sequences at each end was amplified by PCR using specific primers (Table 2) from human genomic DNA. The fragments were inserted into adenoviral and lentiviral vectors at XhoI and EcoRI sites, as previously described (4, 5). The control vector was constructed with a random genomic DNA insert with a length of approximately 500 bp that did not contain any known lncRNAs, microRNAs, or mRNAs.

shRNA vectors: All of the shRNAs were designed by the BLOCK-iT™ RNAi Designer software from Invitrogen (Grand Island, NY). shRNAs were inserted into the lentiviral pSIH-H1 vector (System Biosciences, Mountain View, CA), which utilizes the H1 promoter to drive shRNA expression. The shRNA sequences are listed in Table 2. A control vector containing scrambled shRNA was purchased from System Biosciences (Mountain View, CA).

FENDRR promoter vector: The 5'-flanking region of FENDRR (−1653 to +90) was amplified by PCR using specific primers (Table 2) from human genomic DNA. The fragments were inserted into the luciferase reporter vector pGL3-Basic (Catalog #E1751, Promega, Madison, WI).

miR-214 sensor vector: DNA containing four copies of the miR-214 binding site was inserted downstream of the firefly luciferase gene using the pmirGLO Dual-Luciferase miRNA Target Expression Vector (Promega, Madison, WI) at the Nhe I and Sal I sites. pmirGLO also contains the *renilla* luciferase gene for normalization. The control vector was constructed with a similar-sized random DNA insert that did not contain any known miRNA binding sites. The sensor sequences are listed in Table 2.

All of the inserts in the plasmid constructs described above were confirmed by DNA sequencing.

TABLE 2

Primers for the Construction of Plasmids

| | Human | SEQ ID NO: |
|---|---|---|
| microRNA sensor | | |
| CON-sensor-FW | TCGAGGGGTTCACCGATCCTCCACTGCAGTTGGTTCCGCCAGCAGACGAGAAC TATTTCCTTAAGTTGTGAAGATCTCTTCGGTAGGCCAGCTGGGTTTTAACATG | 41 |
| CON-sensor-RE | AATTCATGTTAAAACCCAGCTGGCCTACCGAAGAGATCTTCACAACTTAAGGA AATAGTTCTCGTCTGCTGGCGGAACCAACTGCAGTGGAGGATCGGTGAACCCC | 42 |
| miR-214-sensor-FW | TCGAGTCTAACTGCCTGTTCCTGCCTGCTGTTATTACTGCCTGTGTGAGCCTG CTGTACATACTGCCTGTCCAGGCCTGCTGTACATACTGCCTGTATTGGCCTGC TGTG | 43 |
| miR-214-sensor-RE | AATTCACAGCAGGCCAATACAGGCAGTATGTACAGCAGGCCTGGACAGGCAGT ATGTACAGCAGGCTCACACAGGCAGTAATAACAGCAGGCAGGAACAGGCAGTT AGAC | 44 |
| FENDRR overexpression | | |
| FENDRR-FW | TTTCTCGAGCAGACAGCGCGGGCTGGGAG | 45 |
| FENDRR-RE | TTTGGTCTCGAATTGTCCATCGAGTTGTCATGCTT | 46 |
| miR-214 overexpression | | |
| miR-214-FW | TATCTCGAGTTCTGTTACGCAAATTATCCATG | 47 |
| miR-214-RE | TCTGAATTCATAGGCACCACTCACTTTACTT | 48 |
| FENDRR promoter | | |
| FENDRR-FW | TGTTGCTAGCGGGAGGAGGAGGAGGAGGAGGAG | 49 |
| FENDRR-RE | TGTTCTCGAGGGCAGGTCTGCGTGCGAGCC | 50 |
| shRNA | | |
| Smad2-shRNA-FW | GATCCGCCTGATCTTCACAGTCATCATTCAAGAGATGATGACTGTGAAGATCA GGCTTTTTG | 51 |
| Smad2-shRNA-RE | AATTCAAAAAGCCTGATCTTCACAGTCATCATCTCTTGAATGATGACTGTGAA GATCAGGCG | 52 |
| Smad3-shRNA-FW | GATCCGCAACCTGAAGATCTTCAACATTCAAGAGATGTTGAAGATCTTCAGGT TGCTTTTTG | 53 |
| Smad3-shRNA-RE | AATTCAAAAAGCAACCTGAAGATCTTCAACATCTCTTGAATGTTGAAGATCTT CAGGTTGCG | 54 |
| FENDRR-shRNA-FW | GATCCGATTTGCCAGCAACTGCATCATTCAAGAGATGATGCAGTTGCTGGCAA ATCTTTTTG | 55 |
| FENDRR-shRNA-RE | AATTCAAAAAGATTTGCCAGCAACTGCATCATCTCTTGAATGATGCAGTTGCT GGCAAATCG | 56 |

TABLE 2-continued

Primers for the Construction of Plasmids

| Human | | SEQ ID NO: |
|---|---|---|
| IRP1-shRNA-FW1 | GATCCGCCATTGGATCCTGTACAACCTTCAAGAGAGGTTGTACAGGATCCAAT GGCTTTTTG | 57 |
| IRP1-shRNA-RE1 | AATTCAAAAAGCCATTGGATCCTGTACAACCTCTCTTGAAGGTTGTACAGGAT CCAATGGCG | 58 |
| IRP1-shRNA-FW2 | GATCCGCAAATTTGTCGAGTTCTTCGTTCAAGAGACGAAGAACTCGACAAATT TGCTTTTTG | 59 |
| IRP1-shRNA-RE2 | AATTCAAAAAGCAAATTTGTCGAGTTCTTCGTCTCTTGAACGAAGAACTCGAC AAATTTGCG | 60 |
| IRP1-shRNA-FW3 | GATCCGCCATTACTAGCTGCACAAACTTCAAGAGAGTTTGTGCAGCTAGTAAT GGCTTTTTG | 61 |
| IRP1-shRNA-RE3 | AATTCAAAAAGCCATTACTAGCTGCACAAACTCTCTTGAAGTTTGTGCAGCTA GTAATGGCG | 62 |

Production of lentiviruses and adenovirus: Lentiviruses were produced using the Lenti-X™ HTX Packaging vectors (Clontech, Mountain View, CA) in HEK 293T cells. For the production of adenovirus, a pENTR vector was switched into the adenoviral vector pAd/PL-DEST using the gateway technique (Invitrogen). The obtained adenoviral vector was linearized by Pac I and transfected into HEK 293A cells to produce virus. Adenovirus was further amplified by re-infecting HEK 293A cells. The adenoviruses were concentrated and purified with the Adenovirus Standard Purification ViralKit™ (VIRAPUR, San Diego). The viral titers were determined by infecting HEK 293T or HEK 293A cells with a series of dilutions of the viral stock and counting the numbers of virus-infected green fluorescent protein (GFP)-positive cells.

Generation of fibroblasts stably expressing FENDRR: Stable cell lines expressing FENDRR were generated using a lentiviral FENDRR vector coupled with puromycin selection. LL29 cells were treated with lentiviral FENDRR or the virus control at a multiplicity of infection (M01) of 50. After 48 hours, cells were selected with puromycin at 0.5 μg/ml for 1 week until they reached confluence, and the medium was changed every two days. The stable cell lines were then cultured with a maintenance concentration of puromycin (0.1 μg/ml) and directly used for further experiment. The stable cell lines were used at passages 4-5.

Dual luciferase assay: For the promoter luciferase reporter assay, HPFs and HFL1 cells were seeded onto a 96-well plate at a density of $2 \times 10^4$ cells per well and transfected with 50 ng of the FENDRR promoter reporter vector and TK plasmid (15 ng), which expresses *Renilla* luciferase for normalization, using Lipofectamine™ 2000 (Invitrogen). 24 hours post transfection, cells were treated with TGFβ1 (5 ng/ml). For the miR-214 sensor luciferase assay, 1) HEK293T cells were seeded onto a 96-well plate at a density of $2 \times 10^4$ cells per well and transfected with 5 ng miR-214 sensor and 20, 40, or 60 ng miR-214 expression or control vector and 150 ng FENDRR expression or control vector using Lipofectamine™ 2000. 2) LL29 cells stably expressing FENDRR or control were seeded onto a 96-well plate at a density of $2 \times 10^4$ cells per well and transfected with 50 ng miR-214 sensor or control sensor using Lipofectamine™ 2000. The cells were collected 48 hours after transfection, and firefly and *Renilla* luciferase activities were measured using the Dual-Luciferase® Reporter Assay System (Promega, Madison, WI). The results are presented as the ratio of firefly to *Renilla* luciferase activities.

RNA pulldown and mass spectrometry analysis: FENDRR with the SP6 promoter were PCR-amplified from FENDRR overexpression vector to serve as DNA template. Antisense FENDRR was amplified as a control (Table 3). The DNA templates were in vitro transcribed to obtain FENDRR and control RNA by using an in vitro transcription kit (ThermoFisher Scientific Catalog #AM1330). The RNAs were labeled using a Pierce RNA 3' End Desthiobiotinylation Kit, and the proteins that interacted with the FENDRR RNA were immunoprecipitated using a Pierce Magnetic RNA-Protein Pull-Down Kit (Thermo Scientific Catalog #20163 and 20164). The RNA pull-down protein samples were analyzed by mass spectrometry (LTQ Orbitrap XL).

TABLE 3

Primer Sequences for RNA Pulldown

| Name | Sequence | SEQ ID NO: |
|---|---|---|
| SP6-FENDRR-FW (variant 3) | ATTTAGGTGACACTATAGAAGAGCA GACAGCGCGGGCTG | 63 |
| SP6-FENDRR-RE (variant 3) | ATATCTATATATGCAAATTAGATGT CTAAATCTATATTCG | 64 |
| SP6-anti-sense FENDRR-FW (variant 3) | ATTTAGGTGACACTATAGAAGAGCA AATTAGATGTCTAAATCTATATTC | 65 |
| SP6-anti-sense FENDRR-RE (variant 3) | CAGACAGCGCGGGCTGGGAG | 66 |

RNA immunoprecipitation (RIP) assay: RIP was carried out as described previously (6). Confluent LL29 cells in 10-cm dishes were harvested by trypsin digestion and were lysed in RIP buffer. The cell lysate was centrifuged at 10,000×g for 15 minutes, and the supernatant was collected. Ten μg of rabbit anti-aconitase 1 (ACO1) (also named IRP1) antibodies (catalog no. Ab126595, Abcam, Boston, MA) or IgG control antibodies were added to 50 μl supernatant, and the mixture was incubated overnight with rotation at 4° C. Forty microliters of protein A/G beads were added and incubated at 4° C. for 1 hour with gentle rotation. The beads were washed three times with ice-cold RIP buffer and three times with PBS. The co-precipitated RNAs were isolated from the re-suspended beads in 1 mL Tri Reagents (Molecular Research Center). The amount of FENDRR in the co-precipitated RNAs was determined by real-time PCR and was calculated with the equation $2^{-Ct}$. Enrichment fold was calculated over IgG control.

Cross-linking immunoprecipitation and qPCR (CLIP-qPCR) analysis: CLIP-qPCR was performed as previously described (7). LL29 cells were cultured in 10-cm dishes until confluence. Cross-linking was performed by irradiating the cells on dishes with 150 mJ/cm$^2$ of UVA in Spectrolinker. The cell pellets were resuspended in three volumes (relative to pellet size) of NP-40 lysis buffer (7). Cell lysates were digested with 1 U/μl of RNase T1 (ThermoFisher Scientific Catalog #AM2280) for 2, 4, 8, and 12 min. The samples treated with RNAse T1 for 2 min having RNAs partially digested in the 100- to 300-nt range in 1.5% formaldehyde agarose gel were selected. One ml of cell lysates was added to the Sepharose beads coated with 10 μg of normal IgG or anti-IRP1 (ACO1) antibodies and incubated for 3 hours at 4° C. The beads were washed three times with NP-40 lysis buffer and incubated with 20 units of RNase-free DNase I in 100 μl NP-40 lysis buffer for 15 min at 37° C. The beads were then incubated with 0.1% SDS and 0.5 mg/ml Proteinase K for 15 min at 55° C. RNA was isolated with acidic phenol extraction and ethanol precipitation. Real-time PCR was used to quantify the relative abundance of overlapping segments spanning the FENDRR RNA. For primer design, FENDRR was divided into 200-nt overlapping intervals so that the amplified products covered all of the full-length transcript. The sequences of the primers used for real-time PCR are shown in Table 4.

TABLE 4

Primers for CLIP-qPCR

| Region | Primer name | Primer sequence | SEQ ID NO: |
|---|---|---|---|
| 134-257 | FW1 | CGAAAGGTGGTGCCGAGAG | 67 |
| 134-257 | RE1 | TCCGTTTGCATCCAACATTGT | 68 |
| 195-294 | FW2 | GCACAGACCCAGGATTTGTG | 69 |
| 195-294 | RE2 | CAGAGCTGGTTTTGACAGTGA | 70 |
| 241-382 | FW3 | TGTTGGATGCAAACGGATTTG | 71 |
| 241-382 | RE3 | CCCTCTCTGGTCTTCAGTTTCT | 72 |
| 301-413 | FW4 | TCTTCCGAAGATACCAAGTGAAA | 73 |
| 301-413 | RE4 | GTCAGTTGTGCCAAACTGAGT | 74 |
| 373-511 | FW5 | CCAGAGAGGGTGAGTGGTTTA | 75 |
| 373-511 | RE5 | TGCAGTTCCTGTAGGTCAGAA | 76 |
| 474-587 | FW6 | CCCTGCTCCTCTCGAATTTCT | 77 |
| 474-587 | RE6 | TTTCTGGTTATCTACGACTGCAT | 78 |
| 540-704 | FW7 | CCACTGCATTTTGGCATGATT | 79 |
| 540-704 | RE7 | GCACACTGCTCAGAGAATGTG | 80 |
| 649-768 | FW8 | CCACCAATTGGCTCGATGAG | 81 |

TABLE 4-continued

Primers for CLIP-qPCR

| Region | Primer name | Primer sequence | SEQ ID NO: |
|---|---|---|---|
| 649-768 | RE8 | GTGACCTGTGAGTGGCGATAA | 82 |
| 732-857 | FW9 | CAGAAGCCCCCTCCTGTTATC | 83 |
| 732-857 | RE9 | AAAGAAGCCAAGCCCATTCTG | 84 |
| 837-962 | FW10 | CAGAATGGGCTTGGCTTCTTT | 85 |
| 837-962 | RE10 | AGCCTATGTCCCATCAACAGT | 86 |
| 909-1058 | FW11 | CGTTTGTTCATTTTCACCACCAT | 87 |
| 909-1058 | RE11 | CCTCCAACAGAAATGCATGCA | 88 |
| 1001-1149 | FW12 | CCAGCTGGAGACTGGTATATGT | 89 |
| 1001-1149 | RE12 | GCACCAAATCCTGAGAAAGAAGA | 90 |
| 1086-1227 | FW13 | CAGACCACCCTCAAATTGAGT | 91 |
| 1086-1227 | RE13 | CCAGTTGAGCCTCTGAATGAC | 92 |
| 1204-1345 | FW14 | GCAGTCATTCAGAGGCTCAAC | 93 |
| 1204-1345 | RE14 | CACAGGGCAAGGATACAGAGA | 94 |
| 1312-1445 | FW15 | TCCTCAGCTCACCTCTCTGTA | 95 |
| 1312-1445 | RE15 | AGTGACAGTCTGGGACATCTG | 96 |
| 1419-1549 | FW16 | AGGATTCAGATGTCCCAGACT | 97 |
| 1419-1549 | RE16 | AAGATGATCCCCAACAATGCT | 98 |
| 1496-1642 | FW17 | CAGGAATGGGTGGCATATGC | 99 |
| 1496-1642 | RE17 | TCTGAGCACACAATCCACTCT | 100 |
| 1596-1738 | FW18 | AGGAAGTCCACTATGCTTGCT | 101 |
| 1596-1738 | RE18 | CCTTGATTCACAATGGCTCAGT | 102 |
| 1715-1847 | FW19 | GCACTGAGCCATTGTGAATCA | 103 |
| 1715-1847 | RE19 | CTGGTTTGTGGAGGAGAGAGT | 104 |
| 1812-1933 | FW20 | TTGGATTCCAGGGGCACTCT | 105 |
| 1812-1933 | RE20 | GCCACTCACATTGTTGCTGAA | 106 |
| 1903-2043 | FW21 | GATCCTGCTGTTCAGCAACAA | 107 |
| 1903-2043 | RE21 | ACTGCAAACCAAAAGGTGCTT | 108 |
| 1995-2118 | FW22 | CCGGTCACTTCACGATGACA | 109 |
| 1995-2118 | RE22 | AACTTCTCCAAGCACAAAGTGT | 110 |
| 2071-2246 | FW23 | CGGCTTCAGGAATTCACAGAA | 111 |
| 2071-2246 | RE23 | CCTAGGTTGTCTCCACTGCTA | 112 |
| 2178-2319 | FW24 | GGAGGTCCTGTGTATGAGGAT | 113 |
| 2178-2319 | RE24 | ACTGCTGAACACACTTTTCCT | 114 |
| 2272-2437 | FW25 | GAGCCCTACAGCAGTGAAAG | 115 |
| 2272-2437 | RE25 | ACCTGGGCATTTACCTTCAGA | 116 |
| 2372-2532 | FW26 | GAACTAGGGTAGAGGCACTAGAG | 117 |
| 2372-2532 | RE26 | CCCCCTTTCCTGACTACTTAACT | 118 |

TABLE 4-continued

Primers for CLIP-qPCR

| Region | Primer name | Primer sequence | SEQ ID NO: |
|---|---|---|---|
| 2481-2649 | FW27 | TCACCTGACCTCTGTGTTTACA | 119 |
| 2481-2649 | RE27 | GCATATTCATGGCAGCTGGTA | 120 |
| 2580-2739 | FW28 | AGTCCCCAAAAACAGGTGGAA | 121 |
| 2580-2739 | RE28 | ACAGGCATGTTTTCTTTCCTAGA | 122 |
| 2654-2816 | FW29 | GCTGCTGGCTAGTGATAAATAAC | 123 |
| 2654-2816 | RE29 | CTCTGTGCCCATCTCTACCAT | 124 |
| 2758-2901 | FW30 | AGCTTAGACAAAGATGGGCAAA | 125 |
| 2758-2901 | RE30 | CATTCCCCGGCTTGTAAAGG | 126 |
| 2835-2991 | FW31 | CACAAACAGAAGGCCAAGTGA | 127 |
| 2835-2991 | RE31 | AAAGGTGATGAAGGGCCAGTT | 128 |
| 2949-3085 | FW32 | CTCCGTCAGAGTCTCCAGAAG | 129 |
| 2949-3085 | RE32 | CGTTTTCTGTGGCAACCATAAC | 130 |
| 3007-3174 | FW33 | CAGAACTGGGCAAGAAAATGTTT | 131 |
| 3007-3174 | RE33 | GTTGTCCATCGAGTTGTCATG | 132 |

*The primers detect human FENDRR variant 3.

Iron levels and aconitase activity assay: Iron levels in the fibroblasts and lung tissues were determined by using an Iron Assay Kit purchased from Sigma (Catalog #MAK025) and expressed as nmol/mg protein. Aconitase activity was measured by using an Aconitase Enzyme Activity Microplate Assay Kit purchased from Abcam (Cata #ab109712) according to the manufacturer's instructions and expressed as nmol/min/mg protein.

Gel contraction activity: Gel contraction activities were measured as previously described (8). LL29 cells stably expressing FENDRR or control vector were split into 6-well plates (200,000 cells/well). The cells were treated with TGFβ1 (5 ng/ml) for 72 hours. Then, the cells were mixed with collagen I (MilliporeSigma, Burlington, MA) to a final density of $1\times10^5$ cells per ml and a final concentration of 1 mg/ml of collagen I with or without 5 ng/ml of TGFβ1. Gel images were taken at 24 hours and quantitatively analyzed using Image J software.

Western blotting: Protein samples were separated on 12% SDS-polyacrylamide gels and transferred onto nitrocellulose membranes. Primary antibodies and dilutions used for Western blotting included: rabbit anti-SMAD2 (catalog no. 3122S, 1:1000 dilution, Cell signaling, Beverly, MA); rabbit anti-SMAD3 (catalog no. 9523S, 1:1000 dilution, Cell signaling); rabbit anti-COL1A1 (catalog no. sc-8784-R, lot #J3013, 1:500 dilution, Santa Cruz Biotechnology, California, CA); rabbit anti-COL3A1 (catalog no. sc-8780-R, lot #L1010, 1:500 dilution, Santa Cruz Biotechnology); mouse anti-α-SMA (catalog no. A2547, 1:1000 dilution, Sigma, St Louis, MO); and mouse anti-GAPDH (catalog no. ab181602, 1:4000 dilution, Abcam, Boston, MA). The secondary antibodies (horseradish peroxidase-conjugated Immuno-Pure anti-rabbit or mouse IgG; HOUR+L) were used at a dilution of 1:5000. The blots were developed with Super Signal West Pico Luminol Enhancer solution and Super Signal West Pico Stable Peroxidase solution (ThermoFisher Scientific).

Immunocytochemistry: LL29 cells stably expressing FENDRR or control vector were cultured and maintained with 0.1 µg/ml of puromycin. Cells were split into 8-chamber slides at a density of 4,000 cells per chamber for 24 hours. The cells were stimulated with 5 ng/ml of TGF-β1 for 48 hours, and then the cells were fixed for immunocytochemical analysis with an anti-α-SMA antibody (1:500) (Sigma) and Alexa 546-conjugated second antibody (1:300) (Molecular Probes, Eugene, OR). Nuclei were stained with Hoechst 33342 (2 µg/ml).

A mouse model of bleomycin-induced pulmonary fibrosis: The animal procedures were approved by the Institutional Animal Care and Use Committee at Oklahoma State University. C57BL/6 male mice (8-10 weeks old) were randomly divided into four groups: saline (Sal) and control adenovirus (AdCON), saline and FENDRR adenovirus (Ad-FENDRR), bleomycin (Bleo) and control adenovirus, and bleomycin and FENDRR adenovirus. On day 0, 60 µl of FENDRR or control adenovirus ($5\times10^9$ infectious units (IU) per mouse) were delivered into the lung intranasally. On day 1, 60 µl of bleomycin (1 U per kg body weight) (Sigma cat #B8416-15UN) or saline (Sal) was delivered intranasally. On day 14, respiratory mechanics were determined using the FlexiVent (Scireq, Montreal, Canada). Then, the left lung was collected for RNA, protein and collagen content analyses. The right lung was fixed in 4% paraformaldehyde for histological analysis. The degree of fibrosis in the mouse lung was quantitated using an Ashcroft score in a blinded manner following the published method (9).

Hydroxyproline Assay: The amount of collagen in the lung tissues was determined by the hydroxyproline assay according to the manufacturer's protocol (QuickZyme Biosciences, Netherland) and expressed as µg per mg lung tissue.

Statistical analysis: The data presented in the figures represent the means±standard error (SEM). Statistical analyses were performed using Student's t-test for two-group comparisons, and Analysis of variance (ANOVA), followed by Tukey's HSD test or Fisher's LSD test, for multiple comparisons. A p-value<0.05 was considered to be significant.

Results

FENDRR is down-regulated in fibrotic lungs and fibroblasts.

There are 2 publicly available RNA_seq datasets from IPF patient lungs: SRA048904, 3 IPF cases and 3 controls (34), and GSE52463, 8 IPFs and 7 controls (35). To identify dysregulated lncRNAs in the lungs of IPF patients, the datasets were re-analyzed for lncRNA expression. 174 (80 up and 94 down) and 56 (6 up and 50 down) dysregulated lncRNAs in IPF lungs were identified from the SRA048904 and GSE52463 datasets, respectively. Of these, 7 down-regulated and zero up-regulated lncRNAs were shared between the 2 datasets (FIG. 1, panel A; Table 5). FENDRR was selected for further studies for the following reasons: (i) FENDRR, but not other lncRNAs (except LINC00961) is conserved between humans and mice; (ii) FENDRR had the fifth and third highest expression among all of the lncRNAs in normal human lungs and human pulmonary fibroblasts (HFPs) (data not shown); and (iii) FENDRR is known to be essential for lung development (21, 23).

TABLE 5

| Seven Common Differentially Expressed lncRNAs in IPF Lungs in the 2 Datasets | | | | | | | |
|---|---|---|---|---|---|---|---|
| | SRA048904 dataset | | | | GSE52463 dataset | | |
| Gene name | Control | IPF | P value | Gene name | Control | IPF | P value |
| RP11-253E3.3 | 28.11 | 13.37 | 0.00165 | RP11-253E3.3 | 11.07 | 4.08 | 0.0007 |
| RP11-38P22.2 | 17.53 | 8.01 | 0.00080 | RP11-38P22.2 | 30.14 | 6.44 | 0.00005 |
| LINC00961 | 38.11 | 15.44 | 0.00025 | LINC00961 | 11.74 | 3.06 | 0.0006 |
| AC093110.3 | 107.91 | 40.01 | 0.00005 | AC093110.3 | 121.79 | 41.46 | 0.00025 |
| FENDRR | 344.53 | 89.47 | 0.00845 | FENDRR | 147.76 | 29.19 | 0.00005 |
| RP1-249H1.4 | 8.86 | 1.94 | 0.00005 | RP1-249H1.4 | 5.70 | 1.55 | 0.00005 |
| LINC00551 | 18.55 | 2.30 | 0.00005 | LINC00551 | 7.88 | 1.00 | 0.0005 |

The down-regulation of FENDRR in the lungs was confirmed using real-time PCR in an independent cohort of 27 patients with IPF from the Lung Tissue Research Consortium (LTRC) and 6 human adult normal lung tissues from BioChain ($0.017 \pm 0.003$ in normal vs. $0.0045 \pm 0.001$ in IPF) (FIG. 1, panel B). Consistent with these findings using human lung tissues, the Fendrr level in mouse lung tissues with bleomycin-induced pulmonary fibrosis was $40.3 \pm 2.4\%$ of the control mouse lungs (FIG. 1, panel C). Fendrr down-regulation was also observed in the fibroblasts, but not in the AEC I and AEC II isolated from the bleomycin-treated mice (FIG. 1, panel D).

Figure 2:
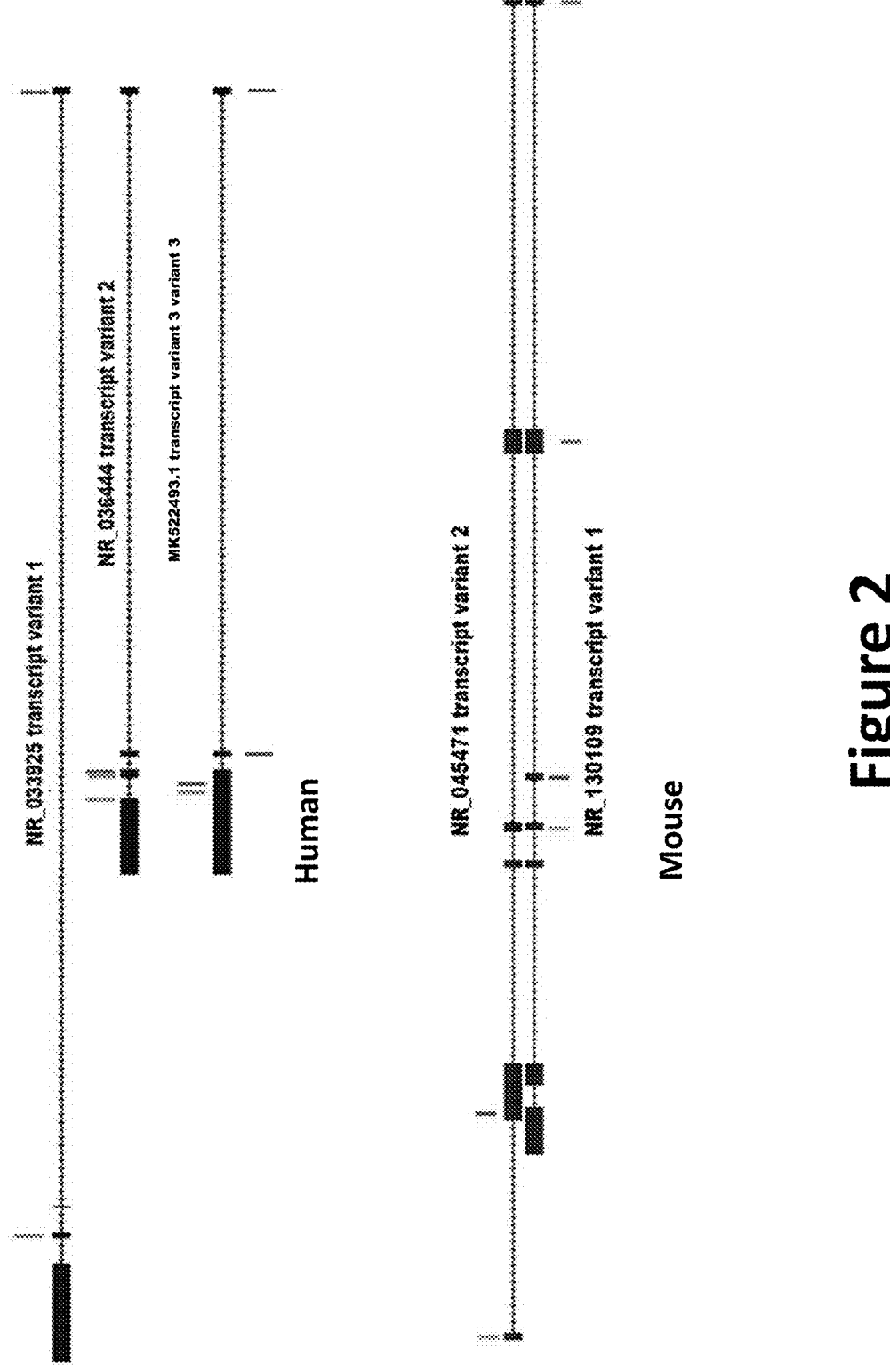
FIG. 2. Gene structure of FENDRR and primer locations used for determining the expression of FENDRR transcript variants. red color: forward primer binding site; and green color: reverse primer binding site. purple color: common primers for human variants 2, 3 and mouse variants 1, 2.

Human FENDRR has two annotated splicing variants, transcript variant 1 (NR_036444; SEQ ID NO:1) and transcript variant 2 (NR_033925; SEQ ID NO:2) in the UCSC Genome Browser (http://genome.ucsc.edu). When it was attempted to clone transcript variant 2 using human lung tissue cDNA, it was found that the cloned FENDRR was 531 bp longer than the transcript variant 2, which is 2,693 bp long (FIG. 2). This was named FENDRR transcript variant 3. The cDNA sequence of variant 3 was submitted to GenBank and assigned the accession number, MK522493.1 (SEQ ID NO:3). Using absolute real-time PCR, it was found that the FENDRR transcript variant 3 was the major transcript in LL29 and HPF fibroblasts (FIG. 1, panel E). Using droplet digit PCR, which provides highly sensitive and absolute quantitation of gene expression, it was found that the FENDRR transcript variant 3 was also the major transcript in normal and IPF human lungs and was reduced in IPF lungs compared to normal lungs (FIG. 1, panel F). Furthermore, variants 1 and 2 were also essentially undetectable in normal and IPF lungs even using the highly sensitive droplet digital PCR technique (FIG. 1, panel F).

There are two mouse Fendrr variants, which are highly homologous (FIG. 2). The variant 1 was expressed much higher than variant 2 in the mouse lungs. Both transcripts were decreased by bleomycin treatment (FIG. 1, panel G). Human FENDRR transcript variant 3 is positionally conserved to mouse Fendrr transcript variant 1 (FIG. 2) and were used for in vivo mouse studies.

Unless noted, a primer pair common to human transcript variants 2 and 3 (FIG. 2 and Table 1) were used for detecting human FENDRR expression in this Example. This primer pair was designed and used before the human FENDRR transcript 3 was discovered. Because the human transcript variant 2 is essentially undetectable in human lungs and human fibroblasts (FIG. 1, panels E and F), this primer pair mainly detects the human transcript variant 3.

TGFβ1 Inhibits FENDRR Expression Via Smad3 in Pulmonary Fibroblasts.

Figure 3:
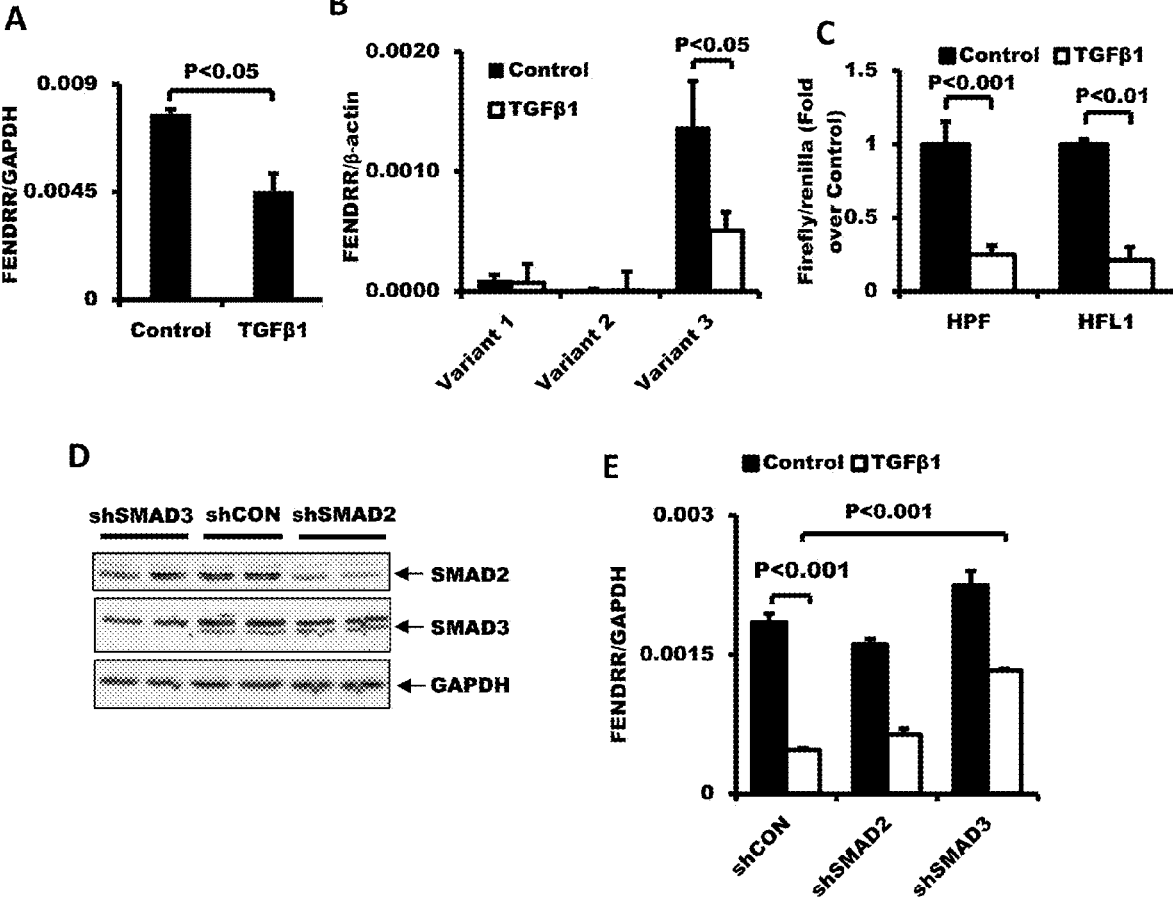
FIG. 3. TGFβ1-SMAD3 signaling inhibits FENDRR expression in lung fibroblasts. Panel (A): Real-time PCR showing FENDRR down-regulation in HPF fibroblasts treated with TGFβ1 (5 ng/ml) for 48 hours (n=3). Panel (B) shows the copy number of FENDRR variants in the control and TGFβ1-treated HPF fibroblasts, as determined by drop-let digital PCR (n=4). Panel (C): Dual luciferase reporter assay showing the inhibition of human FENDRR promoter activity by TGFβ1 in HPF and HFL1 cells. Firefly luciferase activity was normalized to *Renilla* luciferase activity. Fold change was calculated relative to control (n=3). Panel (D): Western blot analysis showing knockdown of SMAD2/3 expression in LL29 cells by shRNA. Panel (E): Real-time PCR showing that FENDRR expression in LL29 cells was inhibited by TGFβ1 and rescued by SMAD3 knockdown (n=3). The results are presented as the means±SEM. Student's t-test for A and ANOVA, followed by Tukey's HSD test for B, C and E.

To assess whether TGFβ regulates FENDRR expression, HPFs were treated with TGFβ1, and FENDRR levels were determined. TGFβ1 reduced FENDRR expression by 42% as measured using the common primer pair to the transcript variants 2 and 3 (FIG. 3, panel A). Similar results were observed using the primer pair specific to the variant 3 and droplet digital PCR (FIG. 3, panel B). Promoter reporter luciferase assays indicated that TGFβ1 decreased the FENDRR promoter activity in primary HPFs and HFL1 fibroblasts (FIG. 3, panel C). Next, it was determined whether the TGFβ1-mediated inhibition of FENDRR expression occurred through Smad transcription factors using RNA interference. The lentiviral shRNA treatment resulted in 79% and 98% decreases in the protein expression levels of Smad2 and Smad3 in LL29 fibroblasts, respectively (FIG. 3, panel D). The silencing of Smad3 but not Smad2 partially reversed the TGFβ1-mediated inhibition of FENDRR expression (FIG. 3, panel E). These results indicate that TGFβ1-SMAD3 signaling contributes to the down-regulation of FENDRR in fibrotic lungs.

FENDRR Inhibits Fibroblast Activation

Figure 4:
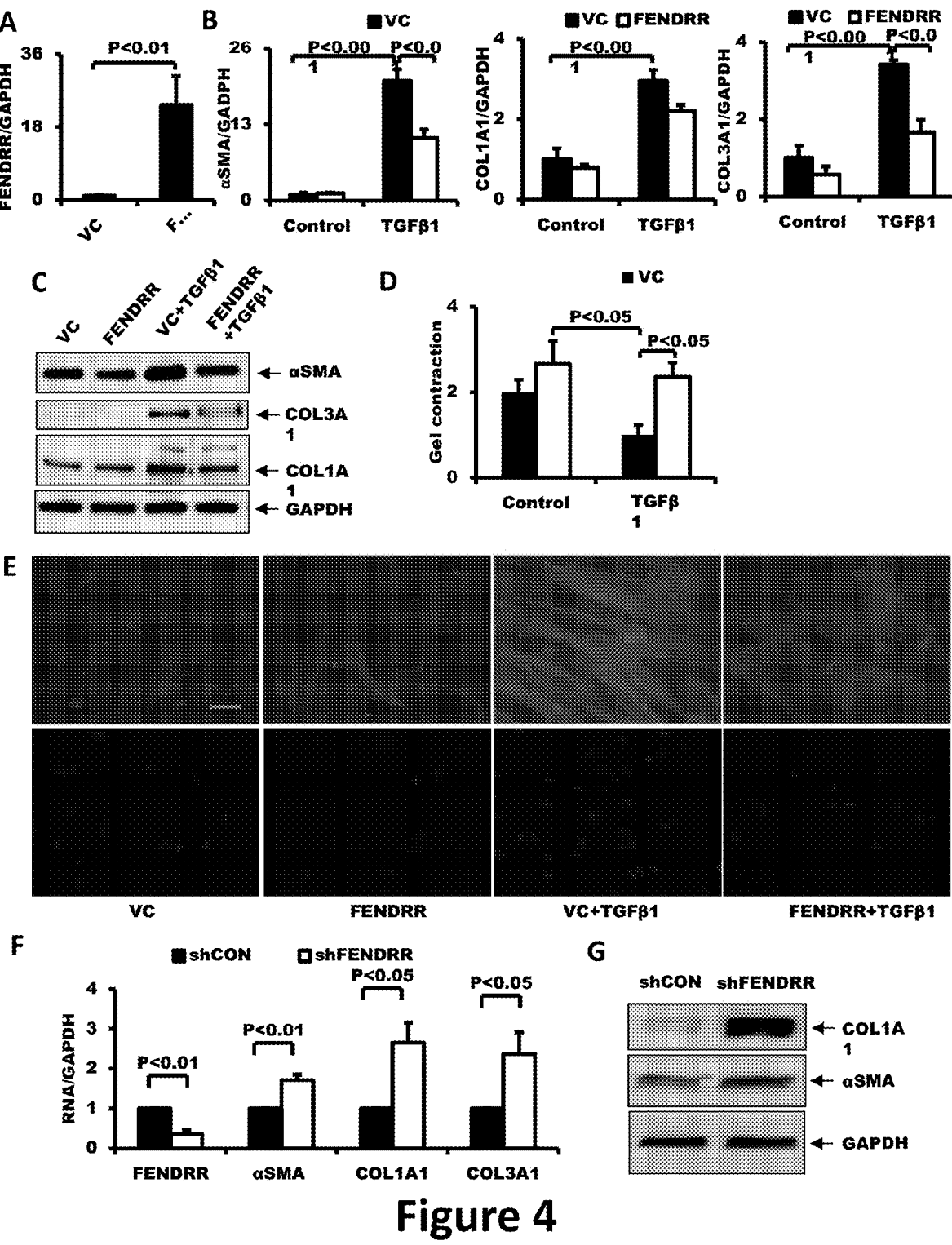
FIG. 4. Overexpression of FENDRR inhibits TGFβ1-induced fibroblast activation. LL29 cells stably expressing FENDRR transcript variant 3 or a control (VC) were treated with 5 ng/ml of TGFβ1 for 48 hours. Panel (A) shows FENDRR expression (n=3). Panel (B) shows that FENDRR overexpression suppressed TGF-β1-induced mRNA expression of α-SMA, COL1A1, and COL3A1. FENDRR and mRNA expression were determined by real-time PCR and normalized to GAPDH (n=3). Panel (C) shows Western blot analysis demonstrating the suppression of TGFβ1-induced α-SMA, COL1A1, and COL3A1 protein expression levels by FENDRR overexpression. Panel (D) shows FENDRR reduced TGFβ1-induced collagen gel contraction. n=4. Panel (E) shows immunostaining demonstrating the inhibition of fiber formation by FENDRR using anti-α-SMA antibodies and Alexa 546-conjugated second antibodies. Scale bar: 50 μm. Panels (F, G): HPF fibroblasts were infected with a lentiviral FENDRR shRNA or its control (shCON) (M01=50) for two days, and the cells were collected for analysis. Real-time PCR and western blotting showing that the knockdown of FENDRR enhanced mRNA expression of α-SMA, COL1A1, and COL3A1 and protein expression of α-SMA and COL1A1. The results are expressed as fold changes relative to shCON. n=3. The results are presented as the means±SEM. Student's t-test for A, F, ANOVA, followed by Tukey's HSD test for B and ANOVA, followed by uncorrected Fisher's LSD test for D.

FENDRR was overexpressed in IPF LL29 fibroblasts using a lentiviral FENDRR (transcript variant 3) vector coupled with puromycin selection to generate stable cell lines and evaluated the effects of FENDRR overexpression on fibroblast activation. A 13-fold increase in FENDRR levels was observed in the FENDRR-overexpressing cells compared to the virus control (VC) cells (FIG. 4, panel A). FENDRR overexpression reduced TGFβ1-induced mRNA and protein expression of α-SMA, COL1A1, and COL3A1 (FIG. 4, panels B and C). Furthermore, FENDRR overexpression reduced TGF-β1-induced contractile activity, as determined by the collagen gel assay and stress fiber formation (FIG. 4, panels D and E). In contrast, knockdown of FENDRR using shRNA increased the mRNA and protein levels of α-SMA and the collagens in HPF normal lung fibroblasts (FIG. 4, panels F and G).

These results indicated that FENDRR inhibits TGFβ-induced fibroblast activation.

FENDRR Interacts with Iron-Responsive Element-Binding Protein 1

As a first step in exploring the mechanisms of FENDRR activity, the subcellular localization of FENDRR was determined by measuring the FENDRR levels in the cytoplasmic and nuclear fractions of primary HPFs and LL29 fibroblasts extracted using a Cytoplasmic & Nuclear RNA Purification Kit. FENDRR in both cells had a low ratio of nuclear to cytoplasmic levels (approximately 0.2), similar to those of cytoplasmic GAPDH and ACTB (β-actin) but in contrast to that of nuclear RNA U2 (>2.5) (FIG. 5, panel A), indicating that FENDRR is primarily located in the cytoplasm of fibroblasts.

Figure 5:
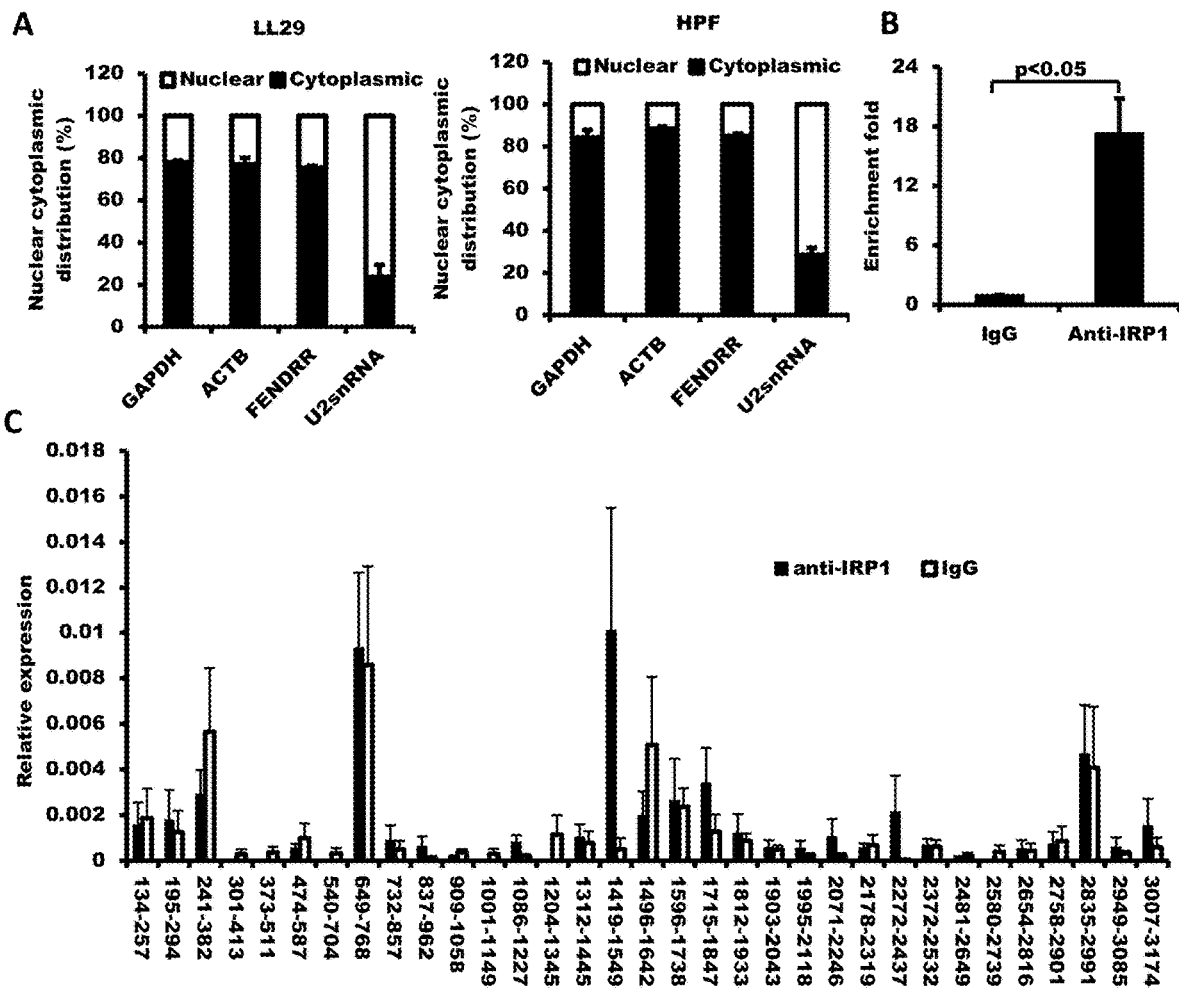
FIG. 5. IRP1 is an interacting partner of FENDRR. Panel (A) shows that FENDRR is preferentially localized in the cytoplasm in fibroblasts. The RNA levels in cytoplasmic and nuclear fractions of LL29 and HPF fibroblasts were determined by real-time PCR and calculated with the equation $2^{-Ct}$. GAPDH, ACTB and U2snRNA were used as controls for cytoplasmic and nuclear RNA, respectively (n=3). Panel (B) shows a RIP assay demonstrating the interaction of FENDRR and IRP1 in LL29 fibroblasts (n=3). Panel (C) shows mapping of the binding region of FENDRR with IRP1 by CLIP-qPCR analysis (n=3). Data are presented as the means±SEM. Student's t-test for B.
Figure 6:
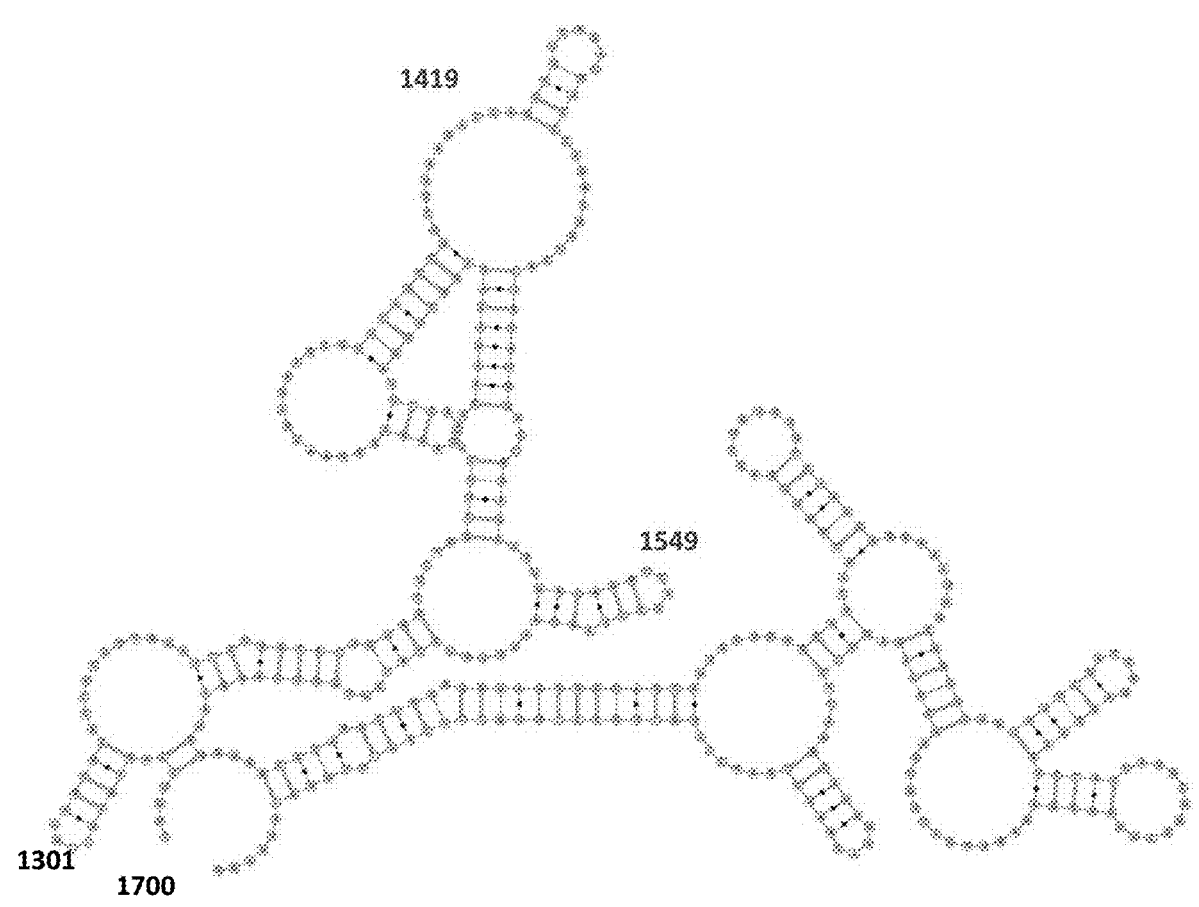
FIG. 6. Predicted RNA structure of FENDRR transcript variant 3. Black color: start and ending position. Red color: start and end positions of the IRP1 binding region.

As a cytoplasmic lncRNA, the inventors hypothesized that FENDRR may perform its functions by interacting with cytoplasmic proteins. To identify such protein partners, RNA pulldown-coupled mass spectrometry analysis was performed. 29 proteins were enriched in the FENDRR pull-down group with a fold change greater than 2 and a FDR value less than 0.05 compared to the control RNA group (Table 6). These proteins included iron-responsive element-binding protein 1 (IRP1) [also named aconitase1 (ACO1)], which controls iron homeostasis by binding to the iron-responsive element (IRE) of mRNAs related to iron transport and storage (36). Since iron overload is associated with fibrosis (37), IRP1 was selected for further study. First, the interaction of IRP1 and FENDRR in lung fibroblasts was validated. RNA immunoprecipitation analysis showed the robust enrichment of FENDRR in an IRP1-interacting RNA fraction compared to that of an IgG control (FIG. 5, panel B). Moreover, CLIP-qPCR analysis was performed to determine the interaction region between FENDRR and IRP1. The results showed that the primary binding region between FENDRR and IRP1 was located at the 1,419-1,549 bp region (FIG. 5, panel C). RNA secondary structures of FENDRR, predicted using IPknot software, are shown in FIG. 6. The region of FENDRR that interacts with IRP1 involves the integration and formation of two independent RNA structures.

FENDRR Controls Iron Levels by Suppressing IRP1

Figure 7:
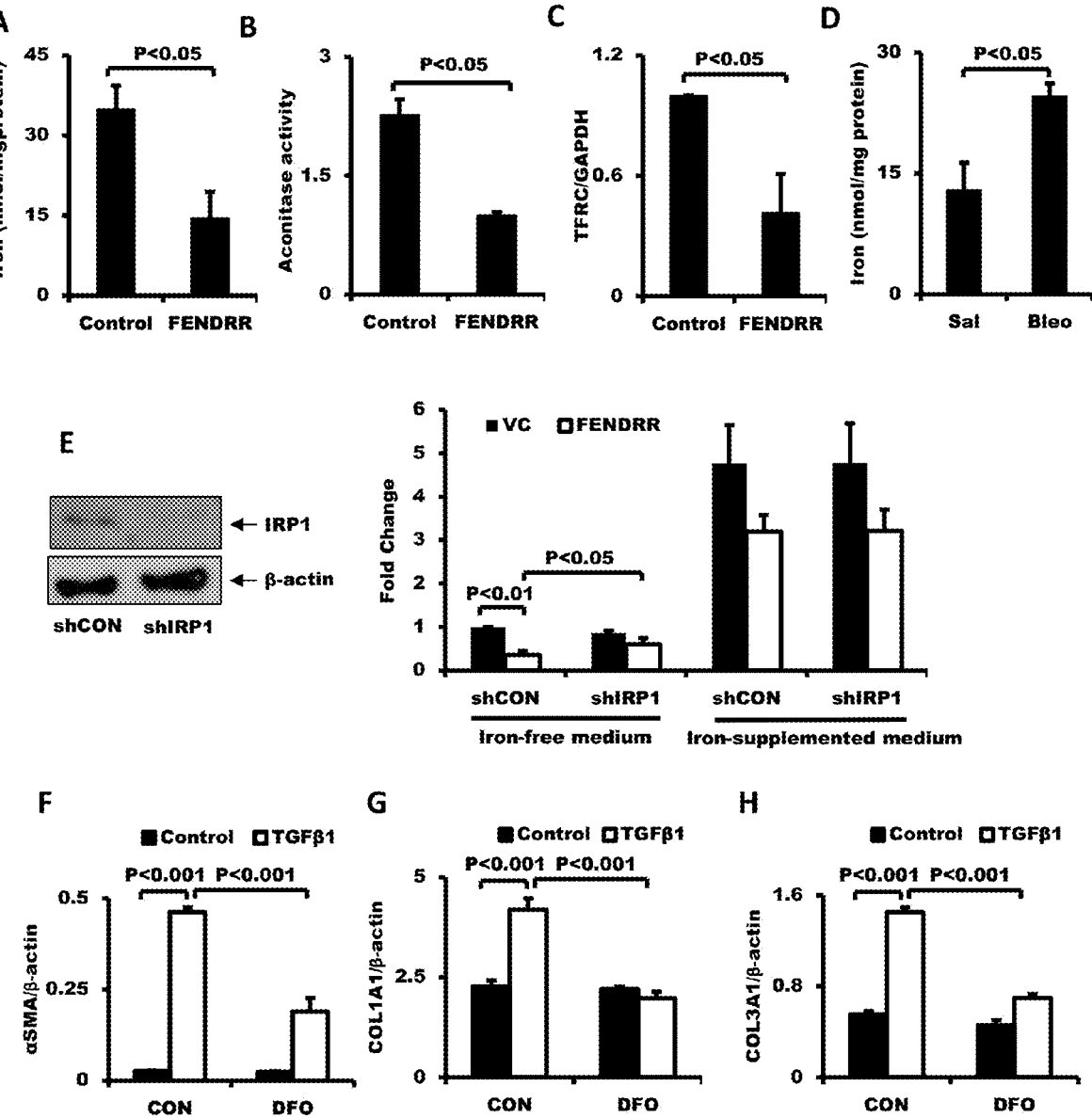
FIG. 7. FENDRR controls iron metabolism by interacting with IRP1. Panel (A) shows that FENDRR overexpression decreased iron levels in LL29 fibroblasts, as determined with an Iron Assay Kit. n=4. Panel (B) shows that FENDRR overexpression inhibited aconitase activity in LL29 fibroblasts, as measured using an Aconitase Enzyme Activity Microplate Assay Kit. n=3. Panel (C) shows real-time PCR demonstrating the suppression of the expression of TFRC mRNA with FENDRR overexpression. n=4. Panel (D) shows that iron levels were increased in primary fibroblasts isolated from the lungs of bleomycin (Bleo)-treated mice compared to that from saline (Sal)-treated mice (n=3). Panel (E): LL29 cells stably expressing FENDRR or a control (VC) were infected with pooled three lentiviral IRP1 shR-NAs or a control (shCON) (M01=50) for two days, and the cells were then cultured in the serum-free RPMI-1640 medium (iron-free medium) or the complete RPMI-1640 medium containing 10 μM ferric ammonium citrate (iron-supplemented medium) for another two days. Western blot-ting shows the knockdown of IRP1 expression. IRP1 knock-down rescued the FENDRR-mediated decrease in cellular iron levels in iron-free medium (n=6). Fold changes were calculated based on the VC and shCON control in the iron-free medium. Panels (F, G, H): LL29 lung fibroblasts were treated with 5 μM desferrioxamine (DFO) and with or without TGFβ1 (5 ng/ml) for 48 hours. The mRNA expression levels of α-SMA, COL1A1 and COL3A1 were deter-mined by real-time PCR (n=3). Data are presented as the means±SEM. Student's t-test for A, B, C and D, ANOVA, followed by uncorrected Fisher's LSD test for E, and ANOVA, followed by Tukey's HSD for F, G, and H.

IRP1 is a dual functional protein, with iron regulatory ability and aconitase activity (36, 38). When cellular iron levels are low, IRP1 binds an iron-responsive element (IRE) in either the 3'-untranslated region (UTR) or 5'-UTR of an mRNA to regulate transport and storage of iron. However, when cellular iron levels are high, IRP1 functions as the cytoplasmic isoform of aconitase to catalyze the interconversion of citrate into isocitrate through cis-aconitate. FENDRR overexpression reduced the iron level in LL29 fibroblasts, as determined using an Iron Assay Kit (FIG. 7, panel A), and the aconitase activity, as measured using an Aconitase Enzyme Activity Microplate Assay (FIG. 7, panel B). IRP1 controls iron homeostasis by binding the IRE of mRNAs related to iron transport and storage, including transferrin receptor 1 (TFRC). FENDRR overexpression reduced TFRC mRNA levels (FIG. 7, panel C). The iron levels in fibroblasts isolated from bleomycin-treated mice were higher than those isolated from control mice (FIG. 7, panel D).

To determine whether FENDRR still regulates cellular iron levels when IRP1 is absent, IRP1 was knocked-down using lentiviral shRNAs, and the effects of IRP1 knock-down on cellular iron levels in the FENDRR-overexpressing

TABLE 6

FENDRR Binding Proteins

| Protein | | Spectrum count of Control | | Spectrum count of FENDRR | | Fold |
| --- | --- | --- | --- | --- | --- | --- |
| Name | Description | Means | SE | Means | SE | change |
| ENOA | Alpha-enolase | 0.00 | 0.00 | 0.74 | 0.74 | N/A |
| IRP1 | iron-responsive element-binding protein 1 (Cytoplasmic aconitate hydratase) | 0.00 | 0.00 | 9.60 | 0.79 | N/A |
| GRSF1 | Isoform 2 of G-rich sequence factor 1 | 0.00 | 0.00 | 2.10 | 0.16 | N/A |
| CNBP | Isoform 2 of Cellular nucleic acid-binding protein | 0.09 | 0.09 | 2.08 | 0.88 | 22.51 |
| ACINU | Apoptotic chromatin condensation inducer in the nucleus | 0.19 | 0.09 | 2.70 | 1.36 | 14.44 |
| FXR2 | Fragile X mental retardation syndrome-related protein 2 | 0.37 | 0.37 | 2.78 | 1.31 | 7.53 |
| ZO1 | Isoform Short of Tight junction protein ZO-1 | 0.19 | 0.09 | 1.40 | 0.55 | 7.51 |
| HNRH3 | Isoform 2 of Heterogeneous nuclear ribonucleoprotein H3 | 0.37 | 0.19 | 2.73 | 0.66 | 7.30 |
| SRSF9 | Serine/arginine-rich splicing factor 9 | 0.93 | 0.49 | 6.53 | 0.41 | 7.00 |
| ECI2 | Isoform 2 of Enoyl-CoA delta isomerase 2, mitochondrial | 0.37 | 0.37 | 2.46 | 1.23 | 6.68 |
| RBM25 | RNA-binding protein 25 | 1.03 | 0.56 | 6.65 | 1.06 | 6.49 |
| PRP31 | U4/U6 small nuclear ribonucleoprotein Prp31 | 1.84 | 0.29 | 7.05 | 1.51 | 3.84 |
| CCAR1 | Isoform 2 of Cell division cycle and apoptosis regulator protein 1 | 1.59 | 0.80 | 5.71 | 0.96 | 3.59 |
| SRRM2 | Serine/arginine repetitive matrix protein 2 | 2.20 | 0.59 | 7.10 | 1.04 | 3.22 |
| IBP7 | Isoform 2 of Insulin-like growth factor-binding protein 7 | 1.16 | 0.66 | 3.69 | 0.60 | 3.16 |
| TRA2A | Transformer-2 protein homolog alpha | 3.55 | 1.83 | 10.11 | 0.54 | 2.85 |
| RU17 | U1 small nuclear ribonucleoprotein 70 kDa | 5.98 | 1.11 | 16.81 | 0.03 | 2.81 |
| RBM14 | RNA-binding protein 14 | 4.87 | 1.75 | 12.17 | 2.39 | 2.50 |
| K6PP | 6-phosphofructokinase type C | 1.97 | 1.07 | 4.83 | 1.87 | 2.45 |
| RNPS1 | RNA-binding protein with serine-rich domain 1 | 1.28 | 0.65 | 3.07 | 0.39 | 2.41 |
| DHE3 | Glutamate dehydrogenase 1, mitochondrial | 4.66 | 1.35 | 11.19 | 0.90 | 2.40 |
| FHL2 | Four and a half LIM domains protein 2 | 3.73 | 2.23 | 8.78 | 3.60 | 2.35 |
| SRSF4 | Serine/arginine-rich splicing factor 4 | 3.71 | 0.82 | 8.72 | 0.77 | 2.35 |
| HNRH1 | Heterogeneous nuclear ribonucleoprotein H | 2.35 | 0.74 | 5.50 | 0.93 | 2.34 |
| PURB | Transcriptional activator protein Pur-beta | 2.72 | 0.62 | 6.20 | 1.20 | 2.28 |
| SNR40 | U5 small nuclear ribonucleoprotein 40 kDa protein | 1.88 | 0.64 | 4.22 | 1.32 | 2.25 |
| BUB3 | Isoform 2 of Mitotic checkpoint protein BUB3 | 3.43 | 1.12 | 7.42 | 1.81 | 2.17 |
| GRP75 | Stress-70 protein, mitochondrial | 2.21 | 1.12 | 4.72 | 1.57 | 2.13 |
| SRPK2 | Isoform 2 of SRSF protein kinase 2 | 3.16 | 0.87 | 6.52 | 2.35 | 2.06 | fibroblasts was examined. IRP1 protein expression was effectively reduced by a pool of three IRP1 shRNAs (FIG. 7, panel E). Then, cellular iron levels in FENDRR-overexpressed and IRP1-knocked down fibroblasts was measured in the iron-free medium, where IRP1 binds with iron metabolism mRNAs, and the iron-supplemented medium, where IRP1 exists in a free form in cytoplasm. In the iron-free medium, FENDRR reduced cellular iron levels by 64%, and the knock-down of IRP1 rescued FENDRR-mediated reduction in cellular iron levels (FIG. 7, panel E). However, in the iron-supplemented medium, FENDRR reduced only 33% of cellular iron levels, and there were no differences in cellular iron levels between control shRNA and IRP1 knockdown conditions. These results indicate that FENDRR likely competes with the binding of IRP1 to iron metabolism genes under a low cellular iron level.

Iron is Required for Fibroblast Activation

Iron overload has been shown to be associated with lung, liver, and renal fibrosis (37, 39). Therefore, the effects of iron on lung fibroblast activation were evaluated. Iron depletion by treatment with the iron chelator desferrioxamine (DFO) suppressed the TGFβ1-induced mRNA expression of α-SMA, COL1A1, and COL3A1 in human lung LL29 fibroblasts (FIG. 7, panels F-H). These results indicated that iron is required for TGFβ-induced fibroblast activation.

FENDRR Competes with Pro-Fibrotic miR-214

Figure 9:
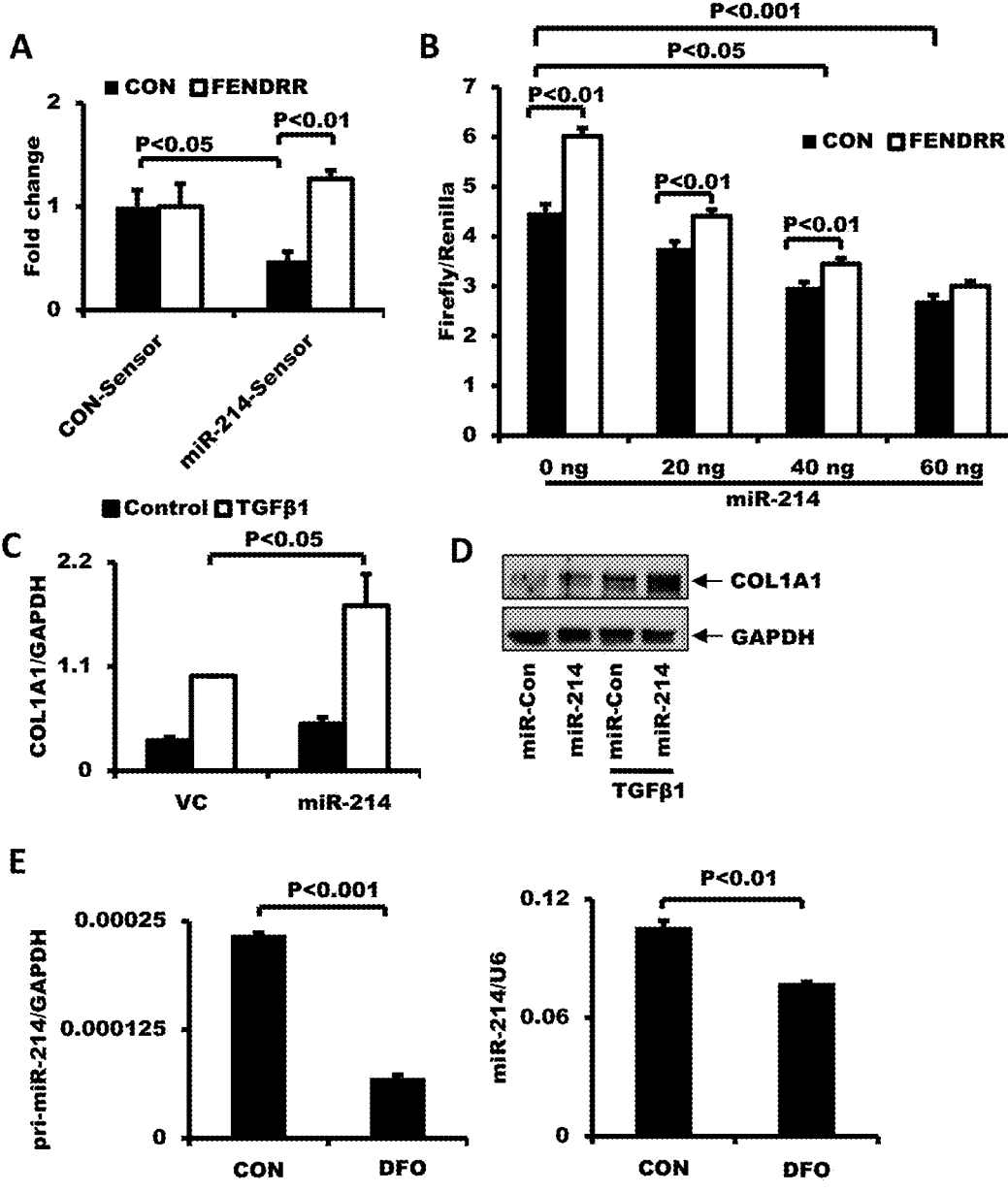
FIG. 9. FENDRR sponges miR-214. Panel (A) shows a luciferase assay showing that FENDRR overexpression increased the activity of miR-214 sensor in LL29 cells (n=4). Panel (B) shows a luciferase assay showing that FENDRR increased miR-214 sensor activity by competing with miR-214 in HEK293T cells. The effects of FENDRR on a miR-214 sensor were reversed by increasing the miR-214 level. HEK293T cells were co-transfected with 5 ng miR-214 sensor and 20, 40, or 60 ng miR-214/Control and 150 ng FENDRR-overexpression vector/control. Luciferase activities were determined 48 hours after trans-fection (n=4). Panels (C, D) show Real-time PCR and western blot analysis demonstrating increases in TGF-β1-induced COL1A1 mRNA and protein levels by miR-214 overexpression. LL29 cells were treated with a lentiviral miR-214 or the virus control (VC) at an MOI of 50 for 48 hours. Then, the cells were stimulated with 5 ng/ml of TGF-β1 for 48 hours (n=4). Panel (E) shows Real-time PCR demonstrating the expression of primary miR-214 (pri-miR214) and mature miR-214 in LL29 cells treated with DFO (n=3). Data are presented as the means±SEM. ANOVA, followed by uncorrected Fisher's LSD test for A, ANOVA, followed by Tukey's HSD test for B, C and student's t-test for E.

One of the mechanisms for lncRNA function involves sponging of microRNAs. To determine whether FENDRR could act as a competing endogenous RNA (ceRNA) or molecular sponge, RNAhybrid was used to predict potential microRNA binding sites; six binding sites for miR-214-3p on FENDRR were found (1028-1055, 1661-1676, 1876-1914, 2132-2147, 2698-2743, and 3010-3037) (FIG. 8). To validate the predication experimentally, a miR-214 sensor consisting of the firefly luciferase gene and 4 copies of miR-214 binding sites was constructed using the pmirGlo reporter vector. The miR-214 sensor activity was inhibited by endogenous miR-214 in the LL29 fibroblasts, and FENDRR overexpression increased the activity of the miR-214 sensor (FIG. 9, panel A). Then, it was determined whether FENDRR directly competes with miR-214. Transfection of HEK293T cells with a FENDRR expression vector increased the miR-214 sensor activity. However, co-transfection with a miR-214 expression vector reduced the sensor activity in both control and FENDRR overexpression groups in a miR-214-dose-dependent manner (FIG. 9, panel B). These results indicate that FENDRR competes with miR-214.

miR-214 is up-regulated in the fibrotic lung tissues of IPF patients (40) and in other fibrotic tissues (41-43). miR-214 functions as a pro-fibrotic agent in the kidneys, liver, and heart (41-43). miR-214 was overexpressed in LL29 fibroblasts with a lentiviral vector, and the activation of fibroblasts was examined. miR-214 increased TGFβ1-induced COL1A1 mRNA and protein expression (FIG. 9, panels C and D).

Next, the relationship between iron levels and miR-214 expression was determined. Iron depletion reduced primary and mature miR-214 expression in LL29 cells (FIG. 9, panel E), indicating that iron overload increases miR-214 expression.

FENDRR Attenuates Bleomycin-Induced Pulmonary Fibrosis in Mice

Figure 10:
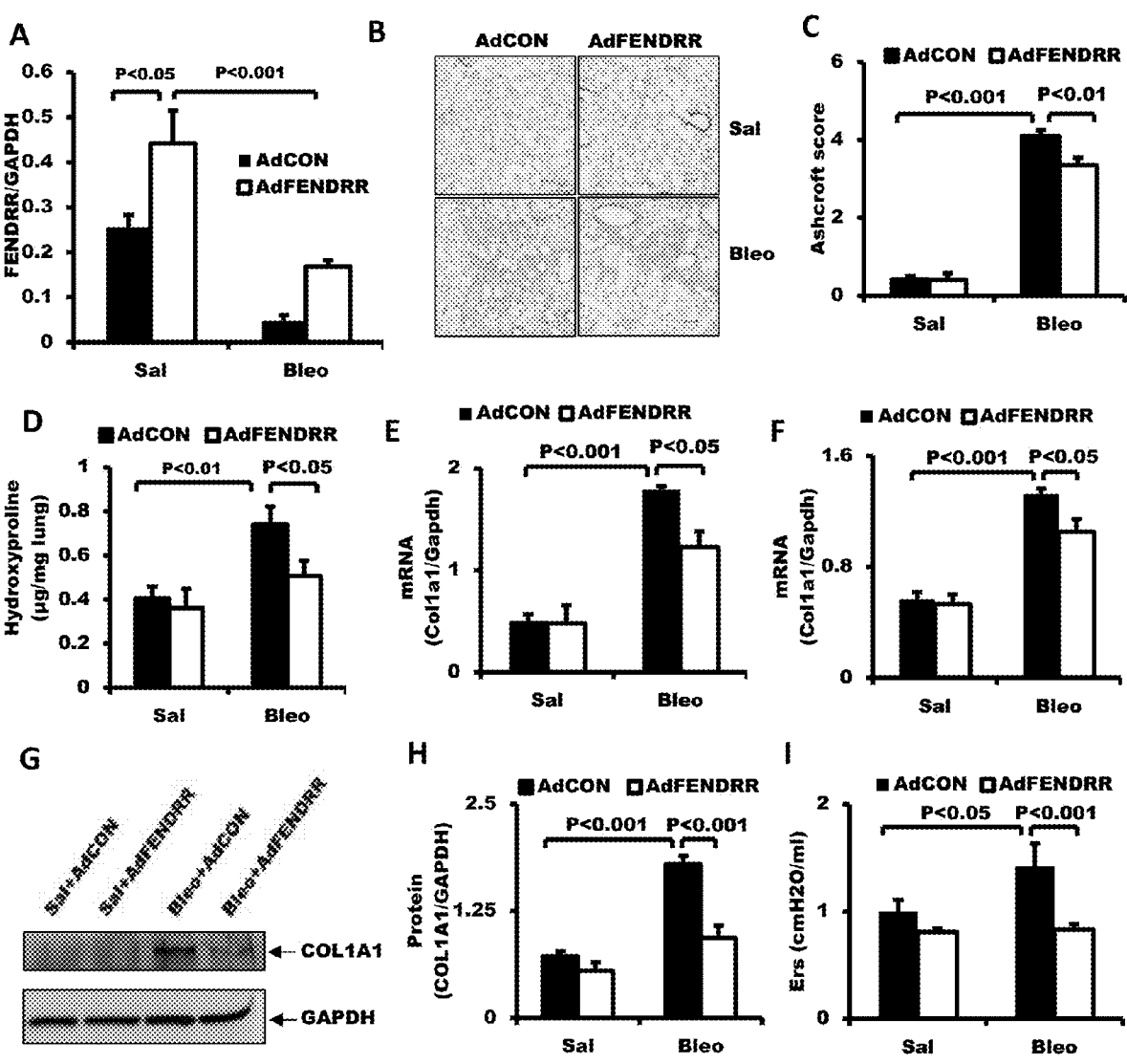
FIG. 10. FENDRR overexpression attenuates bleomycin-induced mouse lung fibrosis. On day 0, mice were infected with AdFENDRR or AdCON ($5 \times 10^9$ IU) through nasal instillation. On day 1, saline (Sal) or bleomycin (Bleo) (1 U/kg BW) was delivered into the mouse lungs through nasal instillation. At D14, the mice were subjected to an analysis of respiratory mechanics by Flexivent and then sacrificed. The left lungs were collected for RNA and protein analysis, and the right lungs were fixed for histological analysis. Panel (A) shows Real-time PCR demonstrating FENDRR overex-pression in mouse lungs. Primers detecting human FENDRR transcript variants 2 and 3 and murine Fendrr transcript variants 1 and 2 were used. Sal+AdCON (n=5), Sal+Ad-FENDRR (n=7), Bleo+AdCON (n=6), Bleo+AdFENDRR (n=8). Panel (B) shows H&E staining demonstrating fibrotic changes in mouse lungs induced by bleomycin. FENDRR attenuated the fibrotic changes in bleomycin-treated mouse lungs. Scale bar: 100 μm. Panel (C) shows Ashcroft score demonstrating that FENDRR lung transfer attenuated bleomycin-induced mouse pulmonary fibrosis. Sal+AdCON (n=15), Sal+AdFENDRR (n=20), Bleo+AdCON (n=21), Bleo+AdFENDRR (n=24). Panel (D) shows a Hydroxyproline assay. Sal+AdCON (n=5), Sal+AdFENDRR (n=7), Bleo+AdCON (n=6), Bleo+AdFENDRR (n=7). Panels (E, F) show Real-time PCR analysis demonstrating that FENDRR inhibited bleomycin-induced Col1a1 and Col3a1 mRNA expression levels in mouse lungs. Sal+AdCON (n=7), Sal+AdFENDRR (n=12), Bleo+AdCON (n=14), Bleo+AdFENDRR (n=16). Panels (G, H) show Western blotting demonstrating that FENDRR inhibited bleomycin-induced COL1A1 protein expression in mouse lungs. Sal+AdCON (n=6), Sal+AdFENDRR (n=6), Bleo+AdCON (n=6), Bleo+AdFENDRR (n=6). Panel (I) shows that FENDRR improved respiratory function in bleomycin-treated mouse by Flexivent analysis. Elastance (Ers) was measured in a single-compartment model. Sal+AdCON (n=6), Sal+AdFENDRR (n=7), Bleo+AdCON (n=6), Bleo+AdFENDRR (n=7). The results are presented as the means±SEM. ANOVA, followed by Tukey's HSD test for A, C, E, F, H and ANOVA, followed by uncorrected Fisher's LSD test for D, I.

Since FENDRR inhibits lung fibroblast activation in vitro, the effects of FENDRR overexpression in mouse lungs on bleomycin-induced pulmonary fibrosis in vivo was examined. Adenovirus-mediated gene transfer was also used to overexpress human FENDRR transcript variant 3, which is positionally conserved to mouse fendrr major transcript variant 1. 1.7-fold and 3.5-fold increases in FENDRR expression in the lungs of saline control- and bleomycin-treated mice, respectively, were observed (FIG. 10, panel A). Histopathological analysis showed reduced fibrosis in the FENDRR-treated group (FIG. 10, panel B). Quantitation of lung fibrosis in a blinded manner revealed that increased FENDRR expression significantly decreased the Ashcroft score (FIG. 10, panel C). Furthermore, increased FENDRR expression inhibited lung collagen levels, as measured by hydroxyproline assay (FIG. 10, panel D), and reduced bleomycin-induced COL1A1 and COL3A1 mRNA expression (FIG. 10, panels E and F) and protein expression of COL1A1 (FIG. 10, panels G and H). FENDRR also decreased elastance (Ers), indicating an improvement in lung function (FIG. 10, panel I).

Discussion

Figure 11:
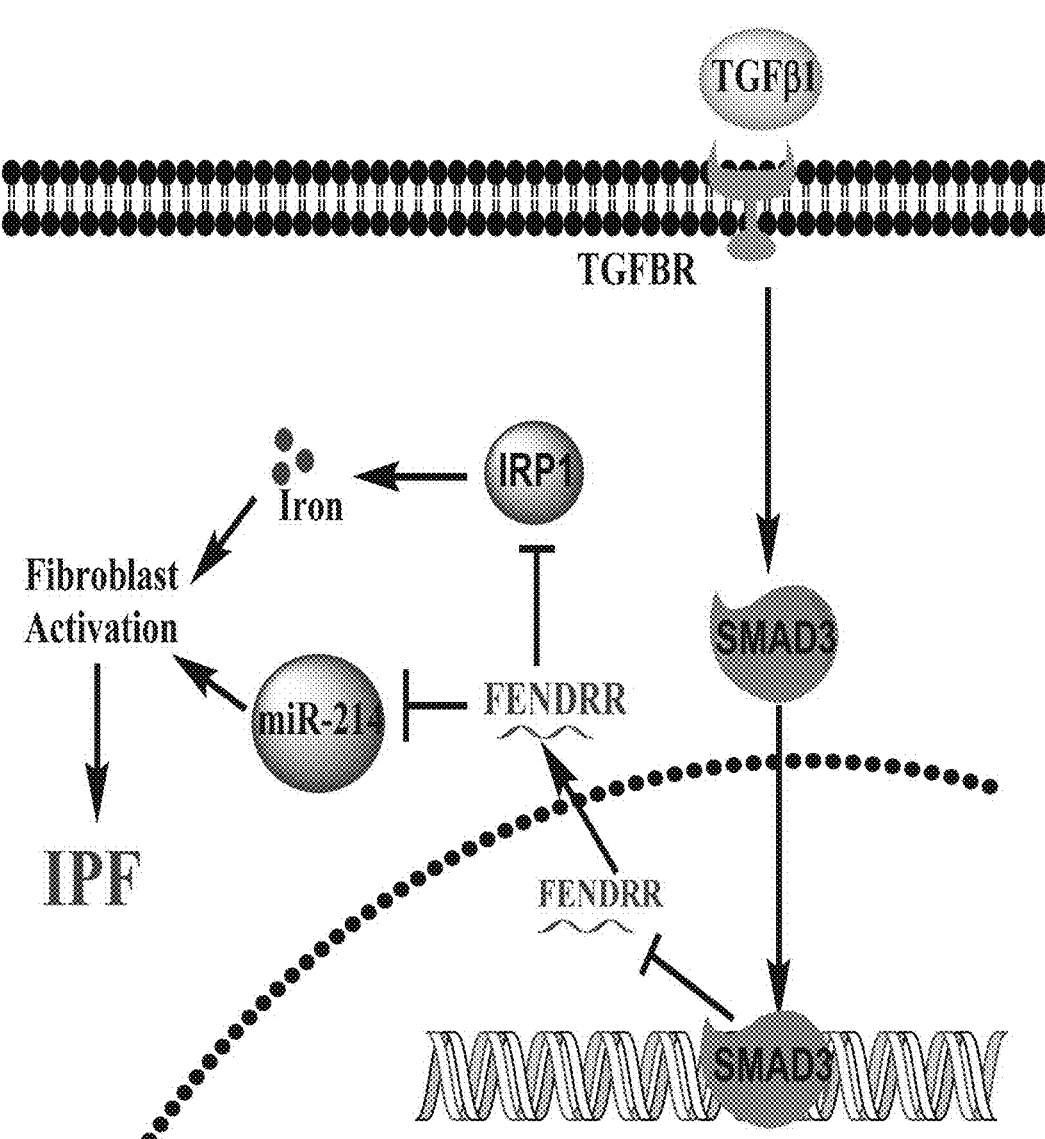
FIG. 11. Schematic representation of one, non-limiting mechanistic model for the regulation of FENDRR in idiopathic pulmonary fibrosis.

Currently, idiopathic pulmonary fibrosis remains a serious human disease. The lack of clarity surrounding the pathogenesis of IPF has resulted in a lack of effective treatments. In the current study, it was discovered that FENDRR was down-regulated in the fibrotic lungs of IPF patients and bleomycin-treated mice. FENDRR expression was regulated by TGF-β/Smad3 signaling. Functionally, FENDRR reduced pulmonary fibrosis by inhibiting fibroblast activation through decreasing cellular iron level via interactions with IRP1 and acting as a ceRNA for profibrotic miR-214 (FIG. 11).

Fendrr is highly expressed in the adult lung compared with other tissues, and it is confined to the mesenchyme in the developing lungs at E14.5 and E18.5 (44). However, at E9.5, Fendrr is restricted to the caudal end of the lateral plate mesoderm (22). How FENDRR is regulated remains unknown. In the present Example, it was found that FENDRR is down-regulated in fibrotic fibroblasts via TGFβ1-SMAD3 signaling. Down-regulation of FENDRR has also been observed in gastric cancer (24). TGFβ-SMAD2/3 signaling has been shown to contribute to the pathogenesis of pulmonary fibrosis (45-47). Our current studies demonstrated that TGFβ1 inhibited FENDRR promoter activity. Furthermore, knockdown of Smad3, but not Smad2, reversed TGFβ1-mediated reduction of FENDRR expression, supporting that TGFβ1-SMAD3 signaling contributes to the FENDRR down-regulation by TGFβ1.

Among non-coding RNAs, microRNAs have been extensively studied in IPF. However, little is known regarding the roles of lncRNAs in IPF. In this Example, FENDRR was found to have anti-fibrotic functions. In in vitro studies, it was revealed that FENDRR inhibited TGF-β-induced fibroblast activation, as demonstrated by the inhibition of collagen synthesis; reduced α-SMA mRNA and protein expression; and decreased contractile activity and stress fiber formation. It is noted that FENDRR overexpression had little effects on these parameters under the basal conditions (without TGFβ). The possible explanation is that FENDRR may regulate the factors involved in the TGFβ signal pathway.

In in vivo studies, this Example further revealed that adenovirus-mediated FENDRR overexpression reduced collagen content and fibrosis in the lungs in response to bleomycin and improved pulmonary function. Pulmonary fibroblasts express low levels of Coxsackie-virus and adenovirus receptor (CAR). It raises a question whether adenovirus can deliver a gene to fibroblasts. It has been reported that adenoviral vector can be used to deliver ET1 or Fas to mouse and human lung fibroblasts in vitro, respectively (48, 49). Thus, it is possible that this may occur in vivo. However, the possibility that FENDRR is also delivered to the respiratory epithelial cells, which in turn affects pulmonary fibroblasts, was not excluded.

The inventors discovered that FENDRR was preferentially localized in the cytoplasm of adult lung fibroblasts. FENDRR has been previously shown to predominantly localize in the nucleus during murine lung development (22). However, cellular localization of lncRNAs can be changed under different physiological conditions. For example, lncRNA GAS5 translocates from the cytoplasm into the nucleus with the glucocorticoid receptor in response to dexamethasone treatment (50). Thus, shifting of FENDRR between the nucleus and cytoplasm might occur during development.

In a previous study, FENDRR was shown to function in development via epigenetic control mechanisms (20). FENDRR increased the PRC2 occupancy by forming dsDNA/RNA triplexes at target regulatory elements (20). Here, a novel mechanism of FENDRR activity in inhibiting fibroblast activation was demonstrated, i.e., regulating cellular iron levels. Iron is a trace element indispensable for nearly all living organisms, as it participates in a variety of biological processes, including electron transport (51, 52), oxygen transport (53), and DNA synthesis (54). However, excessive iron can result in tissue damage due to the formation of free radicals (55, 56). Abnormal iron homeostasis causes a broad spectrum of human diseases. A number of studies has indicated that iron is associated with pulmonary fibrosis. For example, iron deficiency reduces the severity of bleomycin-induced pulmonary fibrosis in hamsters, possibly due to reduced iron-catalyzed oxygen radical formation, and lipid peroxidation (57). An accumulation of iron after silica instillation causes fibrotic lung injury in rats (58). Mobilization of iron from asbestos with a high percentage of iron can enhance collagen production in rat lung fibroblasts (59). Case studies have shown that interstitial lung disease might be linked to exposure to metal dust (60, 61). Two negative results have also been reported in which the treatment of rats or mice with the iron chelator deferoxamine did not inhibit bleomycin-induced lung fibrosis (62, 63). This lack of effects might have been due to the short period of treatment (62) or, in the long-term study (60 days), with the single dose of bleomycin treatment (63), because single dose bleomycin-induced fibrosis normally resolves spontaneously within 4 weeks of treatment.

This Example proposes that FENDRR inhibits fibroblast activation by reducing iron levels via interacting with IRP1, which was supported by the following observations: (i) IRP1 was identified as the target protein of FENDRR by RNA pulldown-coupled mass spectrometry analysis; (ii) FENDRR overexpression inhibited ACO1 activity, reduced cellular iron levels, and decreased TFRC mRNA expression; and (iii) iron was required for TGFβ-induced fibroblast activation.

How iron regulates lung fibroblast activation is still unclear and needs further studies. A few studies show that iron activates TGFβ signaling. One study shows that iron activates TGFβ signaling by increasing TGFβ RII receptor and the phosphorylation of Smad2 in murine hepatic stellate cells (64). Another study reports that iron chelators inhibit the TGFβ/Smad pathway in prostate and colon cancer cells via the reduction in Smad2 expression and Smad3 phosphorylation due to an increase in N-myc downstream-regulated gene-1 (NDRG1) expression (65). Thus, it is possible that FENDRR reduces iron levels, which in turn inhibits TGFβ signaling.

This Example also demonstrated another new mechanism for FENDRR activity regarding its anti-fibrotic effects, i.e., suppressing pro-fibrotic miR-214 activity by acting as its ceRNA. A growing body of evidence indicates that lncRNAs can act as ceRNAs to sponge microRNAs (66). A previous publication also indicated that lncRNAs function in pulmonary fibrosis by interacting with microRNAs to control fibroblast proliferation and activation (67). Here, it is proposed that FENDRR inhibits fibroblast activation by sponging miR-214. This is supported by the following observations: (i) miR-214 enhanced fibroblast activation; (ii) FENDRR contains six binding sites for miR-214; (iii) FENDRR overexpression increased the activity of a miR-214 sensor; and (iv) FENDRR directly competed with miR-214 to affect miR-214 sensor activity. However, a rescue experiment is desired to address if miR-214 can reverse the anti-fibrotic activity of FENDRR. Furthermore, the relative contributions of iron-IRP1 and miR-214 to FENDRR activities remain to be determined. However, iron depletion reduces miR-214 expression, indicating that these two pathways may cross-talk.

In summary, this Example demonstrated that the lncRNA FENDRR is an antifibrotic lncRNA in the lung. This Example further demonstrated that regulating cellular iron levels and competing with miR-214 are two novel mechanisms underlying FENDRR activity in pulmonary fibroblasts.

Thus, in accordance with the present disclosure, there have been provided compositions, and kits containing same, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A method of treating or reducing the occurrence of idiopathic pulmonary fibrosis in a subject, comprising the step of:

administering a composition to the subject, wherein the composition is selected from the group consisting of:

(i) a composition comprising a Fetal-lethal noncoding developmental regulatory RNA (FENDRR) lncRNA and a pharmaceutically-acceptable carrier, wherein the FENDRR lncRNA is encoded by a sequence comprising at least one of SEQ ID NOS: 1-3 and 133-134; and (ii) a composition comprising a vector and a pharmaceutically-acceptable carrier, wherein the vector comprises a sequence encoding a Fetal-lethal noncoding developmental regulatory RNA (FENDRR) lncRNA, wherein the sequence comprises at least one of SEQ ID NOS: 1-3 and 133-134.

2. The method of claim 1, wherein the composition is administered via a route selected from the group consisting of oral, topical, transdermal, parenteral, subcutaneous, intranasal, intratracheal, intrabronchial, mucosal, intramuscular, intraperitoneal, intravitreal, and intravenous routes.

3. The method of claim 1, wherein in (i), the FENDRR lncRNA is encapsulated in a delivery vehicle, wherein the delivery vehicle is selected from the group consisting of a liposome, a lipoplex, a microvesicle, an exosome, a lipidoid nanoparticle, a polymeric nanoparticle, an inorganic nanoparticle, and a stable nucleic acid particle (SNALP).

4. The method of claim 1, wherein in (ii), the vector is an adenoviral vector, an adeno-associated viral (AAV) vector, an alpha viral vector, a herpes viral vector, a lentiviral vector, a measles viral vector, a pox viral vector, a phage vector, or a retroviral vector.

5. The method of claim 1, wherein in (ii), the vector further comprises an expression control sequence to which the sequence is operably linked.

* * * * *

SEQUENCE LISTING

```
Sequence total quantity: 141
SEQ ID NO: 1            moltype = DNA  length = 2693
FEATURE                 Location/Qualifiers
source                  1..2693
                        mol_type = other DNA
                        organism = Homo sapiens
SEQUENCE: 1
agcagacagc gcgggctggg agcgccggca agggcggccc tcgcgcacct ggctgccagc  60
ccgcaggggg ctcgcacgca gacctgccct tgccacctca gcgctcgggt gcgggctggg  120
ggcggtggag ccacgaaagg tggtgccgag agcggagcgc aggacagcgc aggagccccg  180
gcgcatcgcg gcgcgcacag acccaggatt tgtgaagagg tgacccaaat ttcaagacaa  240
```

```
tgttggatgc aaacggattt gccagcaact gcatcactgt caaaaccagc tctgcccgtg  300
tcttccgaag ataccaagtg aaatacatgt agatgggatt tacatctgaa aaaccaagtg  360
agaaactgaa gaccagagag ggtgagtggt ttactcagtt tggcacaact gaccccaacc  420
tagccctcca tgaggactga gcgcatgaga gatcctgagc cacagccgcc cagccctgct  480
cctctcgaat ttctgaccta caggaactgc aagaagtaat gaaagactgc tgtttaaagc  540
cactgcattt tggcatgatt tgttatgcag tcgtagataa ccagaaaaca tcggatttac  600
attttaagga tttggtgcat gggatgggct cagttgggca gttcttctgt tccatgtgat  660
ggtactgggg ctgcagtcat tcagaggctc aactgggctg aacgtgcaag gtttcttgct  720
cacgtggcca tcagtggtgc tggctgctgt tgggagctcc actggacttc tgtccagagc  780
tcctcagctc acctctctgt atccttgccc tgtgctcag gcttctaaca atacagaggc  840
tggattccaa gaggagggaa ttagaagcgt tcagccttct taagaccagg attcagatgt  900
cccagactgt cactgtattg accggagcat ttacaggcca gcctagtaat ttttccatct  960
tgggcaggaa tgggtggcat atgctggggg taggggtagc attgttgggg atcatctttg  1020
gagctgtgtg ccaaggagta aattgctggg ctgctttcta cctgaggaag tccactatgc  1080
ttgcttgtgg agagtggatt gtgtgctcag agtccacaag gatttaagaa tccgagccct  1140
gctgcccttg cctcagcctg tgcattaggg cccggtggtg agagcactga gccattgtga  1200
atcaaggccc ctccctcgac ctgcatacta acaggccaga agagcttgct tgattttggt  1260
cctaggctcc tgcctgtggg ttggattcca ggggcactct ctcctccaca aaccagacgg  1320
tggcaggtac atcccctcaa tggaaattgc ccacacttca ccctaaagac agatcctgct  1380
gttcagcaac aatgtgagtg gcccacacat ttgtccagca tgaaaccgtt tgcagattcc  1440
tttccagtac acagtcccgt cagccggtca cttcacgatg acagctcctc gaagcacctt  1500
ttggtttgca gttgtgtagc ttagaagtag gagcctgcac ggcttcagga attcacagaa  1560
ggagcacact ttgtgcttgg agaagttaat tataggaata tcctgcaacc tgctgctctg  1620
agcctgtgca cctgggggtgt ttccctggag gtcctgtgta tgaggatact catcagcatg  1680
gggtttggga agcctagcag tggagacaac ctaggtggtc ctctccaggg gagtaggtaa  1740
gagccctaca gcagtgaaaa gcattgaagg aaaagtgtgt tcagcagtgc tcttaatctg  1800
atcagagcag cctgaacaca ttctaaacac agggcattta gaactagggt agaggcacta  1860
gagcaccata gatacaaact cagattctga aggtaaatgc ccaggttcaa atccaagccc  1920
cctcgccaag tgaccatgac tcccccgagt cacctgacct ctgtgtttac atcctcaaag  1980
ttaagtagtc aggaaagggg gcttggggct tgccacatgg atggttgcca ctctcctttg  2040
caaagtgtag tccccaaaaa caggtgggaag agggaagggt ccaattagaa ggccgagtac  2100
cagctgccat gaatatgcca gagctgctgg ctagtgataa ataactgaaa cccaggggga  2160
cagcagagct tgggtgacca tacattctag gaaagaaaac atgcctgttg tcctggcttt  2220
ttatccagct tagacaaaga tgggcaaaga aaataattta gaaaatggta gagatgggca  2280
cagagaaagg gcacggaggg aggcacaaac agaaggccaa gtgatggtgg aggcagacat  2340
tggagaaatg cctttacaag ccgggggaatg ccaaggatgc tggcaaccct gggagtggga  2400
agaacctgga acacaccctc cgtcagagtc tccagaagga actggcccctt catcacctt  2460
cggacttctg gcctccagaa ctgggcaaga aaatgtttct gctgttggag gccatccagc  2520
tggtggtcat ttgttatggt tgccacagaa aacgaatata gatttagaca tctaatttgc  2580
atatatagat atgcatgtgt atttgttaaa taaaagataa agcatgacaa ctcgatggac  2640
aacgttacaa ctcattaaat tgtgttggtt aaaaaaaaaa aaaaaaaaaa aaa  2693
```

SEQ ID NO: 2          moltype = DNA   length = 3099
FEATURE               Location/Qualifiers
source                1..3099
                      mol_type = other DNA
                      organism = Homo sapiens
SEQUENCE: 2

```
agcagacagc gcgggctggg agcgccggca agggcggccc tcgcgcacct ggctgccagc  60
ccgcaggggg ctcgcacgca gacctgccct tgccacctca gcgctcgggt gcgggctggg  120
ggcggtggag ccacgaaagg tggtgccgag agcggagcgc aggacagcgc aggagcccg  180
gcgcatcgcg gcgcgcacag acccaggatt acttcatgca cataaaagaa aacgcaacta  240
cagtggaccc tgaacaacct atggcctgca gccactgaag aatgcttgca taaggagctc  300
ttctctgcac atacccgac acagtgatgg tatcttgcag ctgctgcttc tgtccaaggc  360
actgcagcct actcgtcaaa agcccgaagc ccagctctgc cagcagtgca ctgtgtgctc  420
ttaggaaaca gagaagcaaa gaagttagca agcttgtttt ggcagaagaa aaaacacaaa  480
atacccaacc acagatcctc aaaaatattg ctaagcacta attttgctaa catgttagac  540
agccttcgga tctaggcaat cttgttcctc agctggaaag agttcctgcc agccatgtga  600
ttccaaatcc accctggaca tatggggata atgagaaaat cagctccggc cttccctggc  660
cttccagcca agtgaatggg ggcatcccct ggtgcttcag cccggggccc acccagagga  720
tgctagctgg cctgcagagg cctcaaccat gccctcctgg actcaggtaa gactgaggtt  780
tccatgccct caaaacaatt gttcagacaa aaactcactg cccaggtcaa agtcacagca  840
ccagaaagcc aacctgagga tgaagacaaa gctctttgtt ggcacagtcc cctgatcatt  900
cgaggtcagc atctccatca aaatggaccc aatgctgagg caagaaggag aacatcactg  960
ttaagaaggt aatgagtcac aaatgctatt tcgatggttt tctttgaaag aaatacacag  1020
aaccaaacca atttttaatta aagatcttgt ctttgtaatc aggcagccac aaatgaaggc  1080
aaaactgctt tcatgtggca taatatacac agagctgaac tagtttttccc ataaaagggc  1140
aggttctttt cttcaaataa gaaaagagtt tgttcctaac aatatggggg atgcaacaga  1200
aagctgtctt ttgcaaagta taaaattgca gatcctcccg tggaagccat ttcttgatgc  1260
taaaccaatg cgaacgtttg ccaaacgcac atgcgagccg ggattatcct acccttgag  1320
attagacatg tgatcctgat ttttaagtga aaaacgcagc cagaggccaa ataaacatac  1380
ctacaagtac atcgaaagct caaatggttg agaaatgatt gtaacacacc ccggtgtgta  1440
tttctgagga agaatcaaca tgcacatgga aattgatgtt ttgattttta attttaaaac  1500
gacgacagca ctgaaatacc tcccctaact aggtccactg aaaccagtga ggagataatc  1560
attttcagtt aaatatgcat gtaatttaat aatccacaga tggaaaatgc atttgaggtg  1620
gactgaacac agccaggagt ttttgcttat cgacagcact gaatcctgcc ttgactagag  1680
agactcgtca tgtgatcaac tgtggccaga gggcatcctg cagacagctc ctgtcacacc  1740
acactgacca gactcttatg agtatttaag catcttcagg gaagcgattg actgtcttat  1800
aatggtctta caagtacgga actttattac ctgctaataa tcagagcaca tgatggcaca  1860
```

```
atagaatata cgagtgaagt tctaaatgca aggttgttct tattctgtga gtggcaaaac   1920
tcatgcagtg agcagataaa gctggcagga ggcattggcg ccctaatgct gggcactaac   1980
cacctgcccg gactgcgaat atctgttggg tcctttctat atctggtcta ttctcgtgtt   2040
tgattatatc ctggtggcaa gaatagcaaa atcaactctc cttcctatcc catgtggaga   2100
ggcatgattt gagtcagaga gcattatcct ctctgcgtta tccaacccca tgtcccatga   2160
tgcactttgt agacaagcaa gtgtccctgg tggagaatcc acagccacac atcctcattg   2220
gttgcaagga tcagtgtcca atatctactg ccatgatcat tctcagtttt acatccacag   2280
agcttcatag aattctaaca ccacaggtcc aagtagaggt tttggcctca gagtgggcta   2340
gattccacct ctgacagcag ctgtgggact gtttttccat ctgtaaaatg gagacaagag   2400
tatcacctac ctcatggtgt tggtgggatc gttaaacaga attccgatca tgaaaccctt   2460
agcctgctcc ctgcataggc tgcatgcgct cagtgagcta tggctctgtt tcatgctgac   2520
tttaccatca tgtaagcagt tttaaaaatg ctagaagctt tagtcataga attaccatat   2580
gatacagcct actgcagagt ccagaggctg aggcaggaga gttacttgaa cctgggaggc   2640
ggaggttgca gtgagccaag atcgcgccac tgcactccag cctgggcaac agagtgagat   2700
tctgtctcaa cacaaaaaag aagacatgtg tccccatcac agtatcatac agagtgcttc   2760
cactgcccta aaataccctg tgctcttcct attcatccct ctcttcaacc ccagcaacca   2820
ctgatccttt taccatctcc atggttttgc cttttcccaga atgtcatatt gttggaatca   2880
tacgctatgt agcctttgca aatgggcttc tttcaccgag caatgtgcat tgaaggtgcc   2940
tctatgactt ttcaagggtt gatagctcat tcctttttat tgctaaataa tattccattg   3000
tctgaatgta ccacattttg tttatccatt cacctactaa aggacatctt ggttgcttcc   3060
aagtttgggc aattataaat aaaactgcta taaacattg                          3099
```

SEQ ID NO: 3          moltype = DNA  length = 3224
FEATURE               Location/Qualifiers
source                1..3224
                      mol_type = other DNA
                      organism = Homo sapiens
SEQUENCE: 3

```
agcagacagc gcgggctggg agcgccggca agggcggccc tcgcgcacct ggctgccagc   60
ccgcaggggg ctcgcacgca gacctgccct tgccacctca gcgctcgggt gcgggctggg   120
ggcggtggag ccacgaaagg tggtgccgag agcggagcgc aggacagcgc aggagccccg   180
gcgcatcgcg gcgcgcacag acccaggatt tgtgaagagg tgacccaaat ttcaagacaa   240
tgttggatgc aaacggattt gccagcaact gcatcactgt caaaaccagc tctgcccgtg   300
tcttccgaag ataccaagtg aaatacatgt agatgggatt tacatctgaa aaaccaagtg   360
agaaactgaa gaccagagag ggtgagtggt ttactcagtt tggcacaact gaccccaacc   420
tagccctcca tgaggactga gcgcatgaga gatcctgagc cacagccgcc cagccctgct   480
cctctcgaat ttctgaccta caggaactgc aagaagtaat gaaagactgc tgtttaaagc   540
cactgcattt tggcatgatt tgttatgcag tcgtagataa ccagaaaaca tcggatttac   600
attttaaggt aaacttttta ttgaaacatc acatacacac agagacgtcc accaattggc   660
tcgatgagct ttctcaaagg aaacacattc tctgagcagt gtgcacatcc agacacatca   720
tctccatcct ccagaagccc cctcctgtta tcgccactca caggtcaccc gtctcctgac   780
ttgcagccac agagatagtc ctgcctaatt ctgaacgtgg tacaaacgga atcatacaga   840
atgggcttgg cttctttcac tctgggctgt gtttatgagc atcacccaga ttgctgcatg   900
gaagccatcg tttgttcatt ttcaccacca tagagtattc tactgttgat gggacatagg   960
ctatttattc cttctactgt tgagggacgc atagttattt ccagctggag actggtatat   1020
gtctcttggc taccttctgc atgcatttct gttggaggtt gtttcaggta tctcttaacg   1080
tataacagac caccctcaaa ttgagtcctt gaaacaatta ccattttctt ctttctcagg   1140
atttggtgca tgggatgggc tcagttgggc agttcttctg ttccatgtga tggtactggg   1200
gctgcagtca ttcagaggct caactgggct gaacgtgcaa ggtttcttgc tcacgtggcc   1260
atcagtggtg ctggctgctg ttgggagctc cactggactt ctgtccagag ctcctcagct   1320
cacctctctg tatccttgcc ctgtggctca ggcttctaac aatacagagg ctggattcca   1380
agaggaggga attagaagcg ttcagccttc ttaagaccag gattcagatg tcccagactg   1440
tcactgtatt gaccggagca tttacaggcc agcctagtaa tttttccatc ttgggcagga   1500
atgggtggca tatgctgggg gtaggggtag cattgttggg gatcatcttt ggagctgtgt   1560
gccaaggagt aaattgctgg gctgctttct acctgaggaa gtccactatg cttgcttgtg   1620
gagagtggat tgtgtgctca gagtccacaa ggatttaaga atccgagccc tgctgccctt   1680
gcctcagcct gtgcattagg gcccggtggt gagagcactg agccattgtg aatcaaggcc   1740
cctccctcga cctgcatact aacaggccag aagagcttgc ttgattttgg tcctaggctc   1800
ctgcctgtgg gttggattcc aggggcactc tctcctccac aaaccagacg gtgtgcaggta   1860
catcccctca atggaaattg cccacacttc accctaaaga cagatcctgc tgttcagcaa   1920
caatgtgagt ggcccacaca tttgtccagc atgaaaccgt ttgcagattc ctttccagta   1980
cacagtcccg tcagccggtc acttcacgat gacagctcct cgaagcacct tttggtttgc   2040
agttgtgtag cttagaagta ggagcctgca cggcttcagg aattcacaga aggagcacac   2100
tttgtgcttg gagaagttaa ttataggaat atcctgcaac ctgctgctct gagcctgtgc   2160
acctgggggtg tttccctgga ggtcctgtgt atgaggatac tcatcagcat ggggtttggg   2220
aagcctagca gtgagacaa cctaggtggt cctctccagg ggagtaggta agagccctac   2280
agcagtgaaa agcattgaag gaaaagtgtg ttcagcagtg ctcttaatct gatcagagca   2340
gcctgaacac attctaaaca cagggcattt agaactaggg tagaggcact agagcaccat   2400
agatacaaac tcagattctg aaggtaaatg cccaggttca aatccaagcc ccctcgccaa   2460
gtgaccatga ctccccgag tcacctgacc tctgtgttta catcctcaaa gttaagtagt   2520
caggaaaggg ggcttggggc ttgccacatg gatggttgcc actctccttt gcaaagtgta   2580
gtccccaaaa acaggtggaa gagggaaggg tccaattaga aggccgagta ccagctgcca   2640
tgaatatgcc agagctgctg gctagtgata ataactgaa acccagggggg acagcagagc   2700
ttgggtgacc atacattcta ggaaagaaaa catgcctgtt tctttatccgac   2760
ttagacaaag atgggcaaag aaaataattt agaaaatggt agagatgggc acagagaaag   2820
ggcacgagg gaggcacaaa cagaaggcca agtgatggtg gaggcagaca ttggagaaat   2880
gcctttacaa gccgggggaat gccaaggatg ctggcaaccc tgggagtggg aagaacctgg   2940
aacacaccct ccgtcagagt ctccagaagg aactggccct tcatcacctt tcggacttct   3000
ggcctccaga actgggcaag aaaatgtttc tgctgttgga ggccatccag ctggtggtca   3060
```

-continued

```
tttgttatgg ttgccacaga aaacgaatat agatttagac atctaatttg catatataga   3120
tatgcatgtg tatttgttaa ataaaagata aagcatgaca actcgatgga caacgttaca   3180
actcattaaa ttgtgttggt taaaaaaaaa aaaaaaaaaa aaaa                    3224

SEQ ID NO: 4              moltype = DNA   length = 22
FEATURE                  Location/Qualifiers
source                   1..22
                         mol_type = other DNA
                         organism = Homo sapiens
SEQUENCE: 4
cgcacagacc caggattact tc                                              22

SEQ ID NO: 5              moltype = DNA   length = 23
FEATURE                  Location/Qualifiers
source                   1..23
                         mol_type = other DNA
                         organism = Homo sapiens
SEQUENCE: 5
gctccttatg caagcattct tca                                             23

SEQ ID NO: 6              moltype = DNA   length = 21
FEATURE                  Location/Qualifiers
source                   1..21
                         mol_type = other DNA
                         organism = Homo sapiens
SEQUENCE: 6
ccctgctcct ctcgaatttc t                                               21

SEQ ID NO: 7              moltype = DNA   length = 24
FEATURE                  Location/Qualifiers
source                   1..24
                         mol_type = other DNA
                         organism = Homo sapiens
SEQUENCE: 7
ccatgcacca atccttaaa atgt                                             24

SEQ ID NO: 8              moltype = DNA   length = 21
FEATURE                  Location/Qualifiers
source                   1..21
                         mol_type = other DNA
                         organism = Homo sapiens
SEQUENCE: 8
cagaagcccc ctcctgttat c                                               21

SEQ ID NO: 9              moltype = DNA   length = 21
FEATURE                  Location/Qualifiers
source                   1..21
                         mol_type = other DNA
                         organism = Homo sapiens
SEQUENCE: 9
aagaagccaa gcccattctg t                                               21

SEQ ID NO: 10             moltype = DNA   length = 19
FEATURE                  Location/Qualifiers
source                   1..19
                         mol_type = other DNA
                         organism = Homo sapiens
SEQUENCE: 10
gcgcacagac ccaggattt                                                  19

SEQ ID NO: 11             moltype = DNA   length = 19
FEATURE                  Location/Qualifiers
source                   1..19
                         mol_type = other DNA
                         organism = Homo sapiens
SEQUENCE: 11
acacgggcag agctggttt                                                  19

SEQ ID NO: 12             moltype = DNA   length = 21
FEATURE                  Location/Qualifiers
source                   1..21
                         mol_type = other DNA
                         organism = Homo sapiens
SEQUENCE: 12
cgaagacatc ccaccaatca c                                               21

SEQ ID NO: 13             moltype = DNA   length = 21
FEATURE                  Location/Qualifiers
source                   1..21
```

41 42

-continued

```
                             mol_type = other DNA
                             organism = Homo sapiens
SEQUENCE: 13
cagatcacgt catcgcacaa c                                          21

SEQ ID NO: 14          moltype = DNA   length = 21
FEATURE                Location/Qualifiers
source                 1..21
                       mol_type = other DNA
                       organism = Homo sapiens
SEQUENCE: 14
tggctacttc tcgctctgct t                                          21

SEQ ID NO: 15          moltype = DNA   length = 24
FEATURE                Location/Qualifiers
source                 1..24
                       mol_type = other DNA
                       organism = Homo sapiens
SEQUENCE: 15
ttccagacat ctctatccgc atag                                       24

SEQ ID NO: 16          moltype = DNA   length = 20
FEATURE                Location/Qualifiers
source                 1..20
                       mol_type = other DNA
                       organism = Homo sapiens
SEQUENCE: 16
gtgttgcccc tgaagagcat                                            20

SEQ ID NO: 17          moltype = DNA   length = 21
FEATURE                Location/Qualifiers
source                 1..21
                       mol_type = other DNA
                       organism = Homo sapiens
SEQUENCE: 17
cgcctggata gccacataca t                                          21

SEQ ID NO: 18          moltype = DNA   length = 22
FEATURE                Location/Qualifiers
source                 1..22
                       mol_type = other DNA
                       organism = Homo sapiens
SEQUENCE: 18
gaaggtgaag gtcggagtca ac                                         22

SEQ ID NO: 19          moltype = DNA   length = 22
FEATURE                Location/Qualifiers
source                 1..22
                       mol_type = other DNA
                       organism = Homo sapiens
SEQUENCE: 19
catgggtgga atcatattgg aa                                         22

SEQ ID NO: 20          moltype = DNA   length = 22
FEATURE                Location/Qualifiers
source                 1..22
                       mol_type = other DNA
                       organism = Homo sapiens
SEQUENCE: 20
ggcaccacac cttctacaat ga                                         22

SEQ ID NO: 21          moltype = DNA   length = 22
FEATURE                Location/Qualifiers
source                 1..22
                       mol_type = other DNA
                       organism = Homo sapiens
SEQUENCE: 21
acagcctgga tagcaacgta ca                                         22

SEQ ID NO: 22          moltype = DNA   length = 20
FEATURE                Location/Qualifiers
source                 1..20
                       mol_type = other DNA
                       organism = Homo sapiens
SEQUENCE: 22
catcgcttct cggccttttg                                            20

SEQ ID NO: 23          moltype = DNA   length = 21
FEATURE                Location/Qualifiers
```

```
source                   1..21
                         mol_type = other DNA
                         organism = Homo sapiens
SEQUENCE: 23
tggaggtact gcaataccag g                                          21

SEQ ID NO: 24            moltype = DNA   length = 21
FEATURE                  Location/Qualifiers
source                   1..21
                         mol_type = other DNA
                         organism = Homo sapiens
SEQUENCE: 24
atccggttac tgggcaattt c                                          21

SEQ ID NO: 25            moltype = DNA   length = 21
FEATURE                  Location/Qualifiers
source                   1..21
                         mol_type = other DNA
                         organism = Homo sapiens
SEQUENCE: 25
tctgtgtcct cgcaaaaaca g                                          21

SEQ ID NO: 26            moltype = DNA   length = 20
FEATURE                  Location/Qualifiers
source                   1..20
                         mol_type = other DNA
                         organism = Homo sapiens
SEQUENCE: 26
acagcaggca cagacaggca                                            20

SEQ ID NO: 27            moltype = DNA   length = 21
FEATURE                  Location/Qualifiers
source                   1..21
                         mol_type = other DNA
                         organism = Homo sapiens
SEQUENCE: 27
ccctttcccc ttactctcca a                                          21

SEQ ID NO: 28            moltype = DNA   length = 20
FEATURE                  Location/Qualifiers
source                   1..20
                         mol_type = other DNA
                         organism = Homo sapiens
SEQUENCE: 28
ggatgttctg cacagcaagt                                            20

SEQ ID NO: 29            moltype = DNA   length = 21
FEATURE                  Location/Qualifiers
source                   1..21
                         mol_type = other DNA
                         organism = Mus musculus
SEQUENCE: 29
gaactcagga cctctggaag a                                          21

SEQ ID NO: 30            moltype = DNA   length = 21
FEATURE                  Location/Qualifiers
source                   1..21
                         mol_type = other DNA
                         organism = Mus musculus
SEQUENCE: 30
ggtctgcctt gtcgttttct t                                          21

SEQ ID NO: 31            moltype = DNA   length = 21
FEATURE                  Location/Qualifiers
source                   1..21
                         mol_type = other DNA
                         organism = Mus musculus
SEQUENCE: 31
tgctgaatgg aggcatctac a                                          21

SEQ ID NO: 32            moltype = DNA   length = 21
FEATURE                  Location/Qualifiers
source                   1..21
                         mol_type = other DNA
                         organism = Mus musculus
SEQUENCE: 32
gcttgaaccg tctctccttt g                                          21

SEQ ID NO: 33            moltype = DNA   length = 20
```

-continued

```
FEATURE              Location/Qualifiers
source               1..20
                     mol_type = other DNA
                     organism = Mus musculus
SEQUENCE: 33
cacgatccca ggtggacttg                                          20

SEQ ID NO: 34        moltype = DNA   length = 22
FEATURE              Location/Qualifiers
source               1..22
                     mol_type = other DNA
                     organism = Mus musculus
SEQUENCE: 34
tgcaggagtg aagggtgtct ct                                       22

SEQ ID NO: 35        moltype = DNA   length = 20
FEATURE              Location/Qualifiers
source               1..20
                     mol_type = other DNA
                     organism = Mus musculus
SEQUENCE: 35
acgcatggcc aagaagacat                                          20

SEQ ID NO: 36        moltype = DNA   length = 23
FEATURE              Location/Qualifiers
source               1..23
                     mol_type = other DNA
                     organism = Mus musculus
SEQUENCE: 36
ttgtggcaga tacagatcaa gca                                      23

SEQ ID NO: 37        moltype = DNA   length = 22
FEATURE              Location/Qualifiers
source               1..22
                     mol_type = other DNA
                     organism = Mus musculus
SEQUENCE: 37
cacccttctt catcccactc tt                                       22

SEQ ID NO: 38        moltype = DNA   length = 20
FEATURE              Location/Qualifiers
source               1..20
                     mol_type = other DNA
                     organism = Mus musculus
SEQUENCE: 38
tgacatggtt ctggcttcca                                          20

SEQ ID NO: 39        moltype = DNA   length = 22
FEATURE              Location/Qualifiers
source               1..22
                     mol_type = other DNA
                     organism = Mus musculus
SEQUENCE: 39
ctcgtcccgt agacaaaatg gt                                       22

SEQ ID NO: 40        moltype = DNA   length = 22
FEATURE              Location/Qualifiers
source               1..22
                     mol_type = other DNA
                     organism = Mus musculus
SEQUENCE: 40
tgatggcaac aatctccact tt                                       22

SEQ ID NO: 41        moltype = DNA   length = 106
FEATURE              Location/Qualifiers
misc_feature         1..106
                     note = CON-sensor-FW primer
source               1..106
                     mol_type = other DNA
                     organism = synthetic construct
SEQUENCE: 41
tcgagggggtt caccgatcct ccactgcagt tggttccgcc agcagacgag aactatttcc 60
ttaagttgtg aagatctctt cggtaggcca gctgggtttt aacatg                106

SEQ ID NO: 42        moltype = DNA   length = 106
FEATURE              Location/Qualifiers
misc_feature         1..106
                     note = CON-Sensor-RE primer
source               1..106
```

```
                         mol_type = other DNA
                         organism = synthetic construct
SEQUENCE: 42
aattcatgtt aaaacccagc tggcctaccg aagagatctt cacaacttaa ggaaatagtt    60
ctcgtctgct ggcggaacca actgcagtgg aggatcggtg aacccc                   106

SEQ ID NO: 43          moltype = DNA   length = 110
FEATURE                Location/Qualifiers
misc_feature           1..110
                       note = miR-214-sensor-FW primer
source                 1..110
                       mol_type = other DNA
                       organism = synthetic construct
SEQUENCE: 43
tcgagtctaa ctgcctgttc ctgcctgctg ttattactgc ctgtgtgagc ctgctgtaca    60
tactgcctgt ccaggcctgc tgtacatact gcctgtattg gcctgctgtg               110

SEQ ID NO: 44          moltype = DNA   length = 110
FEATURE                Location/Qualifiers
misc_feature           1..110
                       note = miR-214-sensor-RE primer
source                 1..110
                       mol_type = other DNA
                       organism = synthetic construct
SEQUENCE: 44
aattcacagc aggccaatac aggcagtatg tacagcaggc ctggacaggc agtatgtaca    60
gcaggctcac acaggcagta ataacagcag gcaggaacag gcagttagac               110

SEQ ID NO: 45          moltype = DNA   length = 29
FEATURE                Location/Qualifiers
misc_feature           1..29
                       note = FENDRR-FW primer
source                 1..29
                       mol_type = other DNA
                       organism = synthetic construct
SEQUENCE: 45
tttctcgagc agacagcgcg ggctgggag                                      29

SEQ ID NO: 46          moltype = DNA   length = 35
FEATURE                Location/Qualifiers
misc_feature           1..35
                       note = FENDRR-RE primer
source                 1..35
                       mol_type = other DNA
                       organism = synthetic construct
SEQUENCE: 46
tttggtctcg aattgtccat cgagttgtca tgctt                               35

SEQ ID NO: 47          moltype = DNA   length = 32
FEATURE                Location/Qualifiers
misc_feature           1..32
                       note = miR-214-FW primer
source                 1..32
                       mol_type = other DNA
                       organism = synthetic construct
SEQUENCE: 47
tatctcgagt tctgttacgc aaattatcca tg                                  32

SEQ ID NO: 48          moltype = DNA   length = 31
FEATURE                Location/Qualifiers
misc_feature           1..31
                       note = miR-214-RE primer
source                 1..31
                       mol_type = other DNA
                       organism = synthetic construct
SEQUENCE: 48
tctgaattca taggcaccac tcactttact t                                   31

SEQ ID NO: 49          moltype = DNA   length = 33
FEATURE                Location/Qualifiers
misc_feature           1..33
                       note = FENDRR-FW primer
source                 1..33
                       mol_type = other DNA
                       organism = synthetic construct
SEQUENCE: 49
tgttgctagc gggaggagga ggaggaggag gag                                 33

SEQ ID NO: 50          moltype = DNA   length = 30
```

```
FEATURE              Location/Qualifiers
misc_feature         1..30
                     note = FENDRR-RE primer
source               1..30
                     mol_type = other DNA
                     organism = synthetic construct
SEQUENCE: 50
tgttctcgag ggcaggtctg cgtgcgagcc                                        30

SEQ ID NO: 51        moltype = DNA  length = 62
FEATURE              Location/Qualifiers
misc_feature         1..62
                     note = Smad2-shRNA-FW primer
source               1..62
                     mol_type = other DNA
                     organism = synthetic construct
SEQUENCE: 51
gatccgcctg atcttcacag tcatcattca agagatgatg actgtgaaga tcaggctttt    60
tg                                                                      62

SEQ ID NO: 52        moltype = DNA  length = 62
FEATURE              Location/Qualifiers
misc_feature         1..62
                     note = Smad2-shRNA-RE primer
source               1..62
                     mol_type = other DNA
                     organism = synthetic construct
SEQUENCE: 52
aattcaaaaa gcctgatctt cacagtcatc atctcttgaa tgatgactgt gaagatcagg    60
cg                                                                      62

SEQ ID NO: 53        moltype = DNA  length = 62
FEATURE              Location/Qualifiers
misc_feature         1..62
                     note = Smad3-shRNA-FW primer
source               1..62
                     mol_type = other DNA
                     organism = synthetic construct
SEQUENCE: 53
gatccgcaac ctgaagatct tcaacattca agagatgttg aagatcttca ggttgctttt    60
tg                                                                      62

SEQ ID NO: 54        moltype = DNA  length = 62
FEATURE              Location/Qualifiers
misc_feature         1..62
                     note = Smad3-shRNA-RE primer
source               1..62
                     mol_type = other DNA
                     organism = synthetic construct
SEQUENCE: 54
aattcaaaaa gcaacctgaa gatcttcaac atctcttgaa tgttgaagat cttcaggttg    60
cg                                                                      62

SEQ ID NO: 55        moltype = DNA  length = 62
FEATURE              Location/Qualifiers
misc_feature         1..62
                     note = FENDRR-shRNA-FW primer
source               1..62
                     mol_type = other DNA
                     organism = synthetic construct
SEQUENCE: 55
gatccgattt gccagcaact gcatcattca agagatgatg cagttgctgg caaatctttt    60
tg                                                                      62

SEQ ID NO: 56        moltype = DNA  length = 62
FEATURE              Location/Qualifiers
misc_feature         1..62
                     note = FENDRR-shRNA-RE primer
source               1..62
                     mol_type = other DNA
                     organism = synthetic construct
SEQUENCE: 56
aattcaaaaa gatttgccag caactgcatc atctcttgaa tgatgcagtt gctggcaaat    60
cg                                                                      62

SEQ ID NO: 57        moltype = DNA  length = 62
FEATURE              Location/Qualifiers
misc_feature         1..62
                     note = IRP1-shRNA-FW1 primer
```

-continued

```
source                    1..62
                          mol_type = other DNA
                          organism = synthetic construct
SEQUENCE: 57
gatccgccat tggatcctgt acaaccttca agagaggttg tacaggatcc aatggctttt   60
tg                                                                   62

SEQ ID NO: 58            moltype = DNA   length = 62
FEATURE                  Location/Qualifiers
misc_feature             1..62
                          note = IRP1-shRNA-RE1 primer
source                    1..62
                          mol_type = other DNA
                          organism = synthetic construct
SEQUENCE: 58
aattcaaaaa gccattggat cctgtacaac ctctcttgaa ggttgtacag gatccaatgg   60
cg                                                                   62

SEQ ID NO: 59            moltype = DNA   length = 62
FEATURE                  Location/Qualifiers
misc_feature             1..62
                          note = IRP1-shRNA-FW2 primer
source                    1..62
                          mol_type = other DNA
                          organism = synthetic construct
SEQUENCE: 59
gatccgcaaa tttgtcgagt tcttcgttca agagacgaag aactcgacaa atttgctttt   60
tg                                                                   62

SEQ ID NO: 60            moltype = DNA   length = 62
FEATURE                  Location/Qualifiers
misc_feature             1..62
                          note = IRP1-shRNA-RE2 primer
source                    1..62
                          mol_type = other DNA
                          organism = synthetic construct
SEQUENCE: 60
aattcaaaaa gcaaatttgt cgagttcttc gtctcttgaa cgaagaactc gacaaatttg   60
cg                                                                   62

SEQ ID NO: 61            moltype = DNA   length = 62
FEATURE                  Location/Qualifiers
misc_feature             1..62
                          note = IRP1-shRNA-FW3 primer
source                    1..62
                          mol_type = other DNA
                          organism = synthetic construct
SEQUENCE: 61
gatccgccat tactagctgc acaaacttca agagagtttg tgcagctagt aatggctttt   60
tg                                                                   62

SEQ ID NO: 62            moltype = DNA   length = 62
FEATURE                  Location/Qualifiers
misc_feature             1..62
                          note = IRP1-shRNA-RE3 primer
source                    1..62
                          mol_type = other DNA
                          organism = synthetic construct
SEQUENCE: 62
aattcaaaaa gccattacta gctgcacaaa ctctcttgaa gtttgtgcag ctagtaatgg   60
cg                                                                   62

SEQ ID NO: 63            moltype = DNA   length = 39
FEATURE                  Location/Qualifiers
misc_feature             1..39
                          note = SP6-FENDRR-FW (variant 3) primer
source                    1..39
                          mol_type = other DNA
                          organism = synthetic construct
SEQUENCE: 63
atttaggtga cactatagaa gagcagacag cgcgggctg                           39

SEQ ID NO: 64            moltype = DNA   length = 40
FEATURE                  Location/Qualifiers
misc_feature             1..40
                          note = SP6-FENDRR-RE (variant 3) primer
source                    1..40
                          mol_type = other DNA
                          organism = synthetic construct
```

-continued

```
SEQUENCE: 64
atatctatat atgcaaatta gatgtctaaa tctatattcg                              40

SEQ ID NO: 65           moltype = DNA  length = 49
FEATURE                 Location/Qualifiers
misc_feature            1..49
                        note = SP6-anti-sense FENDRR-FW (variant 3) primer
source                  1..49
                        mol_type = other DNA
                        organism = synthetic construct
SEQUENCE: 65
atttaggtga cactatagaa gagcaaatta gatgtctaaa tctatattc                    49

SEQ ID NO: 66           moltype = DNA  length = 20
FEATURE                 Location/Qualifiers
misc_feature            1..20
                        note = SP6-anti-sense FENDRR-RE (variant 3) primer
source                  1..20
                        mol_type = other DNA
                        organism = synthetic construct
SEQUENCE: 66
cagacagcgc gggctgggag                                                    20

SEQ ID NO: 67           moltype = DNA  length = 19
FEATURE                 Location/Qualifiers
source                  1..19
                        mol_type = other DNA
                        organism = Homo sapiens
SEQUENCE: 67
cgaaaggtgg tgccgagag                                                     19

SEQ ID NO: 68           moltype = DNA  length = 21
FEATURE                 Location/Qualifiers
source                  1..21
                        mol_type = other DNA
                        organism = Homo sapiens
SEQUENCE: 68
tccgtttgca tccaacattg t                                                  21

SEQ ID NO: 69           moltype = DNA  length = 20
FEATURE                 Location/Qualifiers
source                  1..20
                        mol_type = other DNA
                        organism = Homo sapiens
SEQUENCE: 69
gcacagaccc aggatttgtg                                                    20

SEQ ID NO: 70           moltype = DNA  length = 21
FEATURE                 Location/Qualifiers
source                  1..21
                        mol_type = other DNA
                        organism = Homo sapiens
SEQUENCE: 70
cagagctggt tttgacagtg a                                                  21

SEQ ID NO: 71           moltype = DNA  length = 21
FEATURE                 Location/Qualifiers
source                  1..21
                        mol_type = other DNA
                        organism = Homo sapiens
SEQUENCE: 71
tgttggatgc aaacggattt g                                                  21

SEQ ID NO: 72           moltype = DNA  length = 22
FEATURE                 Location/Qualifiers
source                  1..22
                        mol_type = other DNA
                        organism = Homo sapiens
SEQUENCE: 72
ccctctctgg tcttcagttt ct                                                 22

SEQ ID NO: 73           moltype = DNA  length = 23
FEATURE                 Location/Qualifiers
source                  1..23
                        mol_type = other DNA
                        organism = Homo sapiens
SEQUENCE: 73
tcttccgaag ataccaagtg aaa                                                23
```

-continued

```
SEQ ID NO: 74          moltype = DNA   length = 21
FEATURE                Location/Qualifiers
source                 1..21
                       mol_type = other DNA
                       organism = Homo sapiens
SEQUENCE: 74
gtcagttgtg ccaaactgag t                                         21

SEQ ID NO: 75          moltype = DNA   length = 21
FEATURE                Location/Qualifiers
source                 1..21
                       mol_type = other DNA
                       organism = Homo sapiens
SEQUENCE: 75
ccagagaggg tgagtggttt a                                         21

SEQ ID NO: 76          moltype = DNA   length = 21
FEATURE                Location/Qualifiers
source                 1..21
                       mol_type = other DNA
                       organism = Homo sapiens
SEQUENCE: 76
tgcagttcct gtaggtcaga a                                         21

SEQ ID NO: 77          moltype = DNA   length = 21
FEATURE                Location/Qualifiers
source                 1..21
                       mol_type = other DNA
                       organism = Homo sapiens
SEQUENCE: 77
ccctgctcct ctcgaatttc t                                         21

SEQ ID NO: 78          moltype = DNA   length = 23
FEATURE                Location/Qualifiers
source                 1..23
                       mol_type = other DNA
                       organism = Homo sapiens
SEQUENCE: 78
tttctggtta tctacgactg cat                                       23

SEQ ID NO: 79          moltype = DNA   length = 21
FEATURE                Location/Qualifiers
source                 1..21
                       mol_type = other DNA
                       organism = Homo sapiens
SEQUENCE: 79
ccactgcatt ttggcatgat t                                         21

SEQ ID NO: 80          moltype = DNA   length = 21
FEATURE                Location/Qualifiers
source                 1..21
                       mol_type = other DNA
                       organism = Homo sapiens
SEQUENCE: 80
gcacactgct cagagaatgt g                                         21

SEQ ID NO: 81          moltype = DNA   length = 20
FEATURE                Location/Qualifiers
source                 1..20
                       mol_type = other DNA
                       organism = Homo sapiens
SEQUENCE: 81
ccaccaattg gctcgatgag                                           20

SEQ ID NO: 82          moltype = DNA   length = 21
FEATURE                Location/Qualifiers
source                 1..21
                       mol_type = other DNA
                       organism = Homo sapiens
SEQUENCE: 82
gtgacctgtg agtggcgata a                                         21

SEQ ID NO: 83          moltype = DNA   length = 21
FEATURE                Location/Qualifiers
source                 1..21
                       mol_type = other DNA
                       organism = Homo sapiens
SEQUENCE: 83
cagaagcccc ctcctgttat c                                         21
```

-continued

```
SEQ ID NO: 84          moltype = DNA  length = 21
FEATURE                Location/Qualifiers
source                 1..21
                       mol_type = other DNA
                       organism = Homo sapiens
SEQUENCE: 84
aaagaagcca agcccattct g                                          21

SEQ ID NO: 85          moltype = DNA  length = 21
FEATURE                Location/Qualifiers
source                 1..21
                       mol_type = other DNA
                       organism = Homo sapiens
SEQUENCE: 85
cagaatgggc ttggcttctt t                                          21

SEQ ID NO: 86          moltype = DNA  length = 21
FEATURE                Location/Qualifiers
source                 1..21
                       mol_type = other DNA
                       organism = Homo sapiens
SEQUENCE: 86
agcctatgtc ccatcaacag t                                          21

SEQ ID NO: 87          moltype = DNA  length = 23
FEATURE                Location/Qualifiers
source                 1..23
                       mol_type = other DNA
                       organism = Homo sapiens
SEQUENCE: 87
cgtttgttca ttttcaccac cat                                        23

SEQ ID NO: 88          moltype = DNA  length = 21
FEATURE                Location/Qualifiers
source                 1..21
                       mol_type = other DNA
                       organism = Homo sapiens
SEQUENCE: 88
cctccaacag aaatgcatgc a                                          21

SEQ ID NO: 89          moltype = DNA  length = 22
FEATURE                Location/Qualifiers
source                 1..22
                       mol_type = other DNA
                       organism = Homo sapiens
SEQUENCE: 89
ccagctggag actggtatat gt                                         22

SEQ ID NO: 90          moltype = DNA  length = 23
FEATURE                Location/Qualifiers
source                 1..23
                       mol_type = other DNA
                       organism = Homo sapiens
SEQUENCE: 90
gcaccaaatc ctgagaaaga aga                                        23

SEQ ID NO: 91          moltype = DNA  length = 21
FEATURE                Location/Qualifiers
source                 1..21
                       mol_type = other DNA
                       organism = Homo sapiens
SEQUENCE: 91
cagaccaccc tcaaattgag t                                          21

SEQ ID NO: 92          moltype = DNA  length = 21
FEATURE                Location/Qualifiers
source                 1..21
                       mol_type = other DNA
                       organism = Homo sapiens
SEQUENCE: 92
ccagttgagc tctgaatga c                                           21

SEQ ID NO: 93          moltype = DNA  length = 21
FEATURE                Location/Qualifiers
source                 1..21
                       mol_type = other DNA
                       organism = Homo sapiens
SEQUENCE: 93
```

-continued

```
gcagtcattc agaggctcaa c                                                  21

SEQ ID NO: 94              moltype = DNA   length = 21
FEATURE                    Location/Qualifiers
source                     1..21
                           mol_type = other DNA
                           organism = Homo sapiens
SEQUENCE: 94
cacagggcaa ggatacagag a                                                  21

SEQ ID NO: 95              moltype = DNA   length = 21
FEATURE                    Location/Qualifiers
source                     1..21
                           mol_type = other DNA
                           organism = Homo sapiens
SEQUENCE: 95
tcctcagctc acctctctgt a                                                  21

SEQ ID NO: 96              moltype = DNA   length = 21
FEATURE                    Location/Qualifiers
source                     1..21
                           mol_type = other DNA
                           organism = Homo sapiens
SEQUENCE: 96
agtgacagtc tgggacatct g                                                  21

SEQ ID NO: 97              moltype = DNA   length = 21
FEATURE                    Location/Qualifiers
source                     1..21
                           mol_type = other DNA
                           organism = Homo sapiens
SEQUENCE: 97
aggattcaga tgtcccagac t                                                  21

SEQ ID NO: 98              moltype = DNA   length = 21
FEATURE                    Location/Qualifiers
source                     1..21
                           mol_type = other DNA
                           organism = Homo sapiens
SEQUENCE: 98
aagatgatcc ccaacaatgc t                                                  21

SEQ ID NO: 99              moltype = DNA   length = 20
FEATURE                    Location/Qualifiers
source                     1..20
                           mol_type = other DNA
                           organism = Homo sapiens
SEQUENCE: 99
caggaatggg tggcatatgc                                                    20

SEQ ID NO: 100             moltype = DNA   length = 21
FEATURE                    Location/Qualifiers
source                     1..21
                           mol_type = other DNA
                           organism = Homo sapiens
SEQUENCE: 100
tctgagcaca caatccactc t                                                  21

SEQ ID NO: 101             moltype = DNA   length = 21
FEATURE                    Location/Qualifiers
source                     1..21
                           mol_type = other DNA
                           organism = Homo sapiens
SEQUENCE: 101
aggaagtcca ctatgcttgc t                                                  21

SEQ ID NO: 102             moltype = DNA   length = 22
FEATURE                    Location/Qualifiers
source                     1..22
                           mol_type = other DNA
                           organism = Homo sapiens
SEQUENCE: 102
ccttgattca caatggctca gt                                                 22

SEQ ID NO: 103             moltype = DNA   length = 21
FEATURE                    Location/Qualifiers
source                     1..21
                           mol_type = other DNA
                           organism = Homo sapiens
```

-continued

```
SEQUENCE: 103
gcactgagcc attgtgaatc a                                                  21

SEQ ID NO: 104          moltype = DNA   length = 21
FEATURE                 Location/Qualifiers
source                  1..21
                        mol_type = other DNA
                        organism = Homo sapiens
SEQUENCE: 104
ctggtttgtg gaggagagag t                                                  21

SEQ ID NO: 105          moltype = DNA   length = 20
FEATURE                 Location/Qualifiers
source                  1..20
                        mol_type = other DNA
                        organism = Homo sapiens
SEQUENCE: 105
ttggattcca ggggcactct                                                    20

SEQ ID NO: 106          moltype = DNA   length = 21
FEATURE                 Location/Qualifiers
source                  1..21
                        mol_type = other DNA
                        organism = Homo sapiens
SEQUENCE: 106
gccactcaca ttgttgctga a                                                  21

SEQ ID NO: 107          moltype = DNA   length = 21
FEATURE                 Location/Qualifiers
source                  1..21
                        mol_type = other DNA
                        organism = Homo sapiens
SEQUENCE: 107
gatcctgctg ttcagcaaca a                                                  21

SEQ ID NO: 108          moltype = DNA   length = 21
FEATURE                 Location/Qualifiers
source                  1..21
                        mol_type = other DNA
                        organism = Homo sapiens
SEQUENCE: 108
actgcaaacc aaaaggtgct t                                                  21

SEQ ID NO: 109          moltype = DNA   length = 20
FEATURE                 Location/Qualifiers
source                  1..20
                        mol_type = other DNA
                        organism = Homo sapiens
SEQUENCE: 109
ccggtcactt cacgatgaca                                                    20

SEQ ID NO: 110          moltype = DNA   length = 22
FEATURE                 Location/Qualifiers
source                  1..22
                        mol_type = other DNA
                        organism = Homo sapiens
SEQUENCE: 110
aacttctcca agcacaaagt gt                                                 22

SEQ ID NO: 111          moltype = DNA   length = 21
FEATURE                 Location/Qualifiers
source                  1..21
                        mol_type = other DNA
                        organism = Homo sapiens
SEQUENCE: 111
cggcttcagg aattcacaga a                                                  21

SEQ ID NO: 112          moltype = DNA   length = 21
FEATURE                 Location/Qualifiers
source                  1..21
                        mol_type = other DNA
                        organism = Homo sapiens
SEQUENCE: 112
cctaggttgt ctccactgct a                                                  21

SEQ ID NO: 113          moltype = DNA   length = 21
FEATURE                 Location/Qualifiers
source                  1..21
                        mol_type = other DNA
```

```
                            organism = Homo sapiens
SEQUENCE: 113
ggaggtcctg tgtatgagga t                                                 21

SEQ ID NO: 114        moltype = DNA   length = 21
FEATURE               Location/Qualifiers
source                1..21
                      mol_type = other DNA
                      organism = Homo sapiens
SEQUENCE: 114
actgctgaac acacttttcc t                                                 21

SEQ ID NO: 115        moltype = DNA   length = 21
FEATURE               Location/Qualifiers
source                1..21
                      mol_type = other DNA
                      organism = Homo sapiens
SEQUENCE: 115
gagccctaca gcagtgaaaa g                                                 21

SEQ ID NO: 116        moltype = DNA   length = 21
FEATURE               Location/Qualifiers
source                1..21
                      mol_type = other DNA
                      organism = Homo sapiens
SEQUENCE: 116
acctgggcat ttaccttcag a                                                 21

SEQ ID NO: 117        moltype = DNA   length = 23
FEATURE               Location/Qualifiers
source                1..23
                      mol_type = other DNA
                      organism = Homo sapiens
SEQUENCE: 117
gaactagggt agaggcacta gag                                               23

SEQ ID NO: 118        moltype = DNA   length = 23
FEATURE               Location/Qualifiers
source                1..23
                      mol_type = other DNA
                      organism = Homo sapiens
SEQUENCE: 118
ccccctttcc tgactactta act                                               23

SEQ ID NO: 119        moltype = DNA   length = 22
FEATURE               Location/Qualifiers
source                1..22
                      mol_type = other DNA
                      organism = Homo sapiens
SEQUENCE: 119
tcacctgacc tctgtgttta ca                                                22

SEQ ID NO: 120        moltype = DNA   length = 21
FEATURE               Location/Qualifiers
source                1..21
                      mol_type = other DNA
                      organism = Homo sapiens
SEQUENCE: 120
gcatattcat ggcagctggt a                                                 21

SEQ ID NO: 121        moltype = DNA   length = 21
FEATURE               Location/Qualifiers
source                1..21
                      mol_type = other DNA
                      organism = Homo sapiens
SEQUENCE: 121
agtccccaaa aacaggtgga a                                                 21

SEQ ID NO: 122        moltype = DNA   length = 23
FEATURE               Location/Qualifiers
source                1..23
                      mol_type = other DNA
                      organism = Homo sapiens
SEQUENCE: 122
acaggcatgt tttctttcct aga                                               23

SEQ ID NO: 123        moltype = DNA   length = 23
FEATURE               Location/Qualifiers
source                1..23
```

-continued

```
                            mol_type = other DNA
                            organism = Homo sapiens
SEQUENCE: 123
gctgctggct agtgataaat aac                                           23

SEQ ID NO: 124              moltype = DNA  length = 21
FEATURE                     Location/Qualifiers
source                      1..21
                            mol_type = other DNA
                            organism = Homo sapiens
SEQUENCE: 124
ctctgtgccc atctctacca t                                             21

SEQ ID NO: 125              moltype = DNA  length = 22
FEATURE                     Location/Qualifiers
source                      1..22
                            mol_type = other DNA
                            organism = Homo sapiens
SEQUENCE: 125
agcttagaca aagatgggca aa                                            22

SEQ ID NO: 126              moltype = DNA  length = 20
FEATURE                     Location/Qualifiers
source                      1..20
                            mol_type = other DNA
                            organism = Homo sapiens
SEQUENCE: 126
cattccccgg cttgtaaagg                                               20

SEQ ID NO: 127              moltype = DNA  length = 21
FEATURE                     Location/Qualifiers
source                      1..21
                            mol_type = other DNA
                            organism = Homo sapiens
SEQUENCE: 127
cacaaacaga aggccaagtg a                                             21

SEQ ID NO: 128              moltype = DNA  length = 21
FEATURE                     Location/Qualifiers
source                      1..21
                            mol_type = other DNA
                            organism = Homo sapiens
SEQUENCE: 128
aaaggtgatg aagggccagt t                                             21

SEQ ID NO: 129              moltype = DNA  length = 21
FEATURE                     Location/Qualifiers
source                      1..21
                            mol_type = other DNA
                            organism = Homo sapiens
SEQUENCE: 129
ctccgtcaga gtctccagaa g                                             21

SEQ ID NO: 130              moltype = DNA  length = 22
FEATURE                     Location/Qualifiers
source                      1..22
                            mol_type = other DNA
                            organism = Homo sapiens
SEQUENCE: 130
cgttttctgt ggcaaccata ac                                            22

SEQ ID NO: 131              moltype = DNA  length = 23
FEATURE                     Location/Qualifiers
source                      1..23
                            mol_type = other DNA
                            organism = Homo sapiens
SEQUENCE: 131
cagaactggg caagaaaatg ttt                                           23

SEQ ID NO: 132              moltype = DNA  length = 21
FEATURE                     Location/Qualifiers
source                      1..21
                            mol_type = other DNA
                            organism = Homo sapiens
SEQUENCE: 132
gttgtccatc gagttgtcat g                                             21

SEQ ID NO: 133              moltype = DNA  length = 2714
FEATURE                     Location/Qualifiers
```

```
source                 1..2714
                       mol_type = other DNA
                       organism = Mus musculus SEQUENCE: 133
cgggttccgg aaagcgggtg gcgcaggcgg ggagcgcgtc agggagcggc cctggctgcg    60
gggtcgcggc cttggagaga tgatgcgggg cgcaggacga ttcacgatcc caggtggact   120
tgcgcgctcg aaaccagcga tcacagggcc caaatggaaa ccagagagct ccgaataggc   180
cacagcggtc agttacccag gactgcagag acacccttca ctcctgcatg cgtttgatct   240
gactccacca gaaggtccag tcgccaacgc ctagctgagg tcccaggcca ggccttaccc   300
ccaacccta ccctctcagc ctccaattga aagaaggcct gccggctcca actcaattag    360
cacaaaggcg gcggcgggca ccctggtctg tgccgcaggg cagggagcgt cctggcgggc   420
aggtagagag aagtccgcta gccccgggtg ttatcagcaa gcggcttaat caggaatttg   480
agctgacaac gtgcgcaccg ccacccggct ccgccagccg gttgacggtg ggagtgagac   540
ccgagaggct ggagtccag acttcaaagc tgcccgaggt gcggcggcct tggggaaggg    600
ggcgcccggc gacaatcggc aaccccgagc gccgcctgga cagaagccgg cgggccagtg   660
ggcgctggac catcttccct gcgaatacaa tgcagctgtc ttcagacaca cactagaaga   720
gtgcagtgga ctccattaca gatggctgtg agccaccatg tggttgctgg taattgaact   780
caggacctct ggaagagcaa tctgtgctct taactgctga gccacctctc cagttcccac   840
caccaccatg cccgctcggc cccccagaca tcacacaaag aagaaaacga caaggcagac   900
caacagatga acaggatcca gagtgaccag aaccagacca gatgtcccat gatgacatca   960
caggagggac cgacattgtg ggaatggtgc ttgaagatga tggtgacact ttctgggaag  1020
accttcccgg atctccagag gtccaaattt gcatggtgag tcccaacctc caccactggt  1080
ctttgtgccc tcctggtaga gctgtgccct gcccgtgtgg ttataatggg gccatcacat  1140
gtgtgtagag gatgaagaca gccacagtga catgccggac atttattatg catcagtagt  1200
ctccatccac tgtgcccaca gcacccactt gagagtcact cctagctgac atggtacctc  1260
aactggaatc ctctatccaa ggatcttgtg gaccacatag gctaattag aatatgctct   1320
tctctgcggc tgctggtcag ggatgagcgc tctcccatgt ctgcttctgt tagccgtgaa  1380
tgagtctgcc ttcttttta ggaatgaata tatattcttt gatggttcca tacatgtaca  1440
catgtactgt ctgttgatta tattttacgc cacaccctt actccccat gtcttcccaa   1500
aatctcttct ctctcctctc ttctccctcc cctccatcct cttccttctc ctcctcctct  1560
tctttaaaac cacacccagt ccagtgagtg ttgcctgaac acacatgggc attgagccat  1620
cccagggact tgggcaacct accagcagtc atccatacct ttggagaagc tcggccgtcc  1680
ttccttggaa gcatccattg gcctatgacc tccggaccca cagcttttga ctaggtgcat  1740
ggcactagat ttgtgttccc tcctctgaag cagacctcag atcccgtcag aaaacgggtg  1800
gctcccacaa ccaccatgcc tctatggcac tggtagcagg gcttgctttg gctttgttcc  1860
ttaacttcca gctaccttga gatcttctag gcagctcccc tgcagccaga ggaccagcta  1920
ttcagctgcg tgtgacagat gacaatgttc cttcccctac ccgcctgccc acccagagct  1980
ctgacctggt gtcagcctct tgtgctgaat ggaggcatct acagctgctg ggtgagtact  2040
ctgaattccc tgatgtcaaa atgacgctcg ggaatgtgcc agcctcatga gtctgttggt  2100
ctgtctcact cattcactcc atcagctgag ggtgggatcc gaacagatcc ggttatgcat  2160
catgtatatc actgggatgt gtaccgagag tcaccatgga aacctgggta tgggactcag  2220
agtcaccatg gaaaccagcc actgggtatg cctgtcagga agcttctaga gtgtgttcac  2280
ggaagtggga agagccaccc tgcgtgttgg cagtgccatc tcttcgtgat ctggggtcct  2340
ggacagaatg aaaaggagca agcaagtgga gtaccagcag tcacccctct ctgcttcctg  2400
actgtgggtg ccatgtgacc agctgtttca tgttcctgcc actgtgcctc cccgccatga  2460
cggactgtgc acgctcacac tgtgagccag cgcgaaccct tccttcttta aggtgctttt  2520
tgttacagcg gtgagacgac ggctaatatg ctgcagaaac acgtgcacgg tgtgcagggc  2580
tcacgtggac gacacaatcc ctgctgcatc tcatttgact agctctcagc atctgcttca  2640
gccgctcttc taggaaacca ctcttattct tctggactct cttttgctca taaattaaaa  2700
tgcaaattct atca                                                    2714

SEQ ID NO: 134        moltype = DNA  length = 2458
FEATURE               Location/Qualifiers
source                1..2458
                      mol_type = other DNA
                      organism = Mus musculus SEQUENCE: 134
cgggttccgg aaagcgggtg gcgcaggcgg ggagcgcgtc agggagcggc cctggctgcg    60
gggtcgcggc cttggagaga tgatgcgggg cgcaggacga ttcacgatcc caggtggact   120
tgcgcgctcg aaaccagcga tcacagggcc caaatggaaa ccagagagct ccgaataggc   180
cacagcggtc agttacccag gactgcagag acacccttca ctcctgcatg cgtttgatct   240
gactccacca gaaggtccag tcgccaacgc ctagctgagg tcccaggcca ggccttaccc   300
ccaacccta ccctctcagc ctccaattga aagaaggcct gccggctcca actcaattag    360
cacaaaggcg gcggcgggca ccctggtctg tgccgcaggg cagggagcgt cctggcgggc   420
aggtagagag aagtccgcta gccccgggtg ttatcagcaa gcggcttaat caggaatttg   480
agctgacaac gtgcgcaccg ccacccggct ccgccagccg gttgacggtg ggagtgagac   540
ccgagaggct ggagtccag acttcaaagc tgcccgaggt gcggcggcct tggggaaggg    600
ggcgcccggc gacaatcggc aaccccgagc gccgcctgga cagaagccgg cgggccagtg   660
ggcgctggac catcttccct gcgaaacatc acacaaagaa gaaaacgaca aggcagacca   720
acagatgaac aggatccaga gtgaccagaa ccagaccaga tgtcccatga tgacatcaca   780
ggagggaccg acattgtggg aatggtgctt gaagatgatg gtgacacttt ctgggaagac   840
cttcccggat ctccagaggt acggaaccga ggtccaaatt tgcatggtga gtcccaacct   900
ccaccactgg tctttgtgcc ctcctggtag agctgtgccc tgcccgtgtg gttataatgg   960
ggcatcaca tgtgtgtaga ggatgaagac agccacagtg acatgccgga catttattat   1020
gcatcagtag tctccatcca ctgtgcccac agcacccact tgagagtcac tcctagctga  1080
catggtacct caactggaat cctctatcca aggatcttgt ggaccacatg aggctaatta  1140
gaatatgctc ttctctgcgg ctgctggtca gggatgagcg ctctcccatg tctgcttctg  1200
ttagccgtga atgagtctgc cttcttttta ggaatgaata tatattcttt gatggttcc   1260
atacatgtac acatgtactg tctgttgatt atattttacg ccacaccct tactccccca   1320
```

-continued

```
tgtcttccca aaatctcttc tctctcctct cttctccctc ccctccatcc tcttccttct    1380
cctcctcctc ttctttaaaa ccacacccag tccagtgagt gttgcctgaa cacacatggg    1440
cattgagcca tcccagggac ttgggcaacc taccagcagt catccatacc tttggagaag    1500
ctcggccgtc cttccttgga agcatccatt gtaagtagat cttcacccag ggatgggatt    1560
ttatgagcct ctcccgtcca tgctggatat tgactgactc catcgtgtgt gaatcaccac    1620
agctgctgtg agttcgtgaa tccgatgctc acacatcgtg gccagaggac agcatttcac    1680
tcccctctcc cagcctctag ctttgatgtt ctttctgctt cctctcccat aatgtcccct    1740
gagcttcaca ggggataggt ggatataggt gtcccatcag gggtgaacac tcacggtcac    1800
ttactgttag cactttgatc aagccgtgag tcccagcact aaccactaca ctggaagaaa    1860
cagcttcctg agcaatgcta atttatggat ataaatagaa atattgagaa ggcaatttga    1920
cagcgtgtcc atttaaccgg tagtttctcc cctagggcct atgacctccg gacccacagc    1980
ttttgactag gtgcatggca ctagatttgt gttccctcct ctgaagcaga cctcagatcc    2040
cgtcagaaaa cgggtggctc ccacaaccac catgcctcta tggcactggt agcagggctt    2100
gctttggctt tgttccttaa cttccagcta ccttgagatc ttctaggcag ctcccctgca    2160
gccagaggac cagctattca gctgcgtgtg acagatgaca atgttccttc ccctacccgc    2220
ctgcccaccc agagctctga cctggtgtca gcctcttgtg ctgaatggag gcatctacag    2280
ctgctggaaa ttagagcgct ccgttccgtg gtattacgcg gcggcactcc acgggcctgg    2340
gagtgcagag ctgattggat gtcccaccca aaggagagac ggttcaagct ctttccagga    2400
aattgagtgg aacacccaaa ctgacatcca atattaaata ttgtatttgt ggacttgt     2458
```

```
SEQ ID NO: 135         moltype = RNA   length = 28
FEATURE                Location/Qualifiers
source                 1..28
                       mol_type = other RNA
                       organism = Homo sapiens
SEQUENCE: 135
ggctaccttc tgcatgcatt tctgttgg                                         28

SEQ ID NO: 136         moltype = RNA   length = 22
FEATURE                Location/Qualifiers
source                 1..22
                       mol_type = other RNA
                       organism = Homo sapiens
SEQUENCE: 136
acagcaggca cagacaggca gt                                               22

SEQ ID NO: 137         moltype = RNA   length = 15
FEATURE                Location/Qualifiers
source                 1..15
                       mol_type = other RNA
                       organism = Homo sapiens
SEQUENCE: 137
atccgagccc tgctg                                                       15

SEQ ID NO: 138         moltype = RNA   length = 39
FEATURE                Location/Qualifiers
source                 1..39
                       mol_type = other RNA
                       organism = Homo sapiens
SEQUENCE: 138
aattgcccac acttcaccct aaagacagat cctgctgtt                             39

SEQ ID NO: 139         moltype = RNA   length = 16
FEATURE                Location/Qualifiers
source                 1..16
                       mol_type = other RNA
                       organism = Homo sapiens
SEQUENCE: 139
tcctgcaacc tgctgc                                                      16

SEQ ID NO: 140         moltype = RNA   length = 46
FEATURE                Location/Qualifiers
source                 1..46
                       mol_type = other RNA
                       organism = Homo sapiens
SEQUENCE: 140
agcttgggtg accatacatt ctaggaaaga aaacatgcct gttgtc                     46

SEQ ID NO: 141         moltype = RNA   length = 28
FEATURE                Location/Qualifiers
source                 1..28
                       mol_type = other RNA
                       organism = Homo sapiens
SEQUENCE: 141
aactgggcaa gaaaatgttt ctgctgtt                                         28
```